US012318197B2

(12) United States Patent
Sarto et al.

(10) Patent No.: US 12,318,197 B2
(45) Date of Patent: Jun. 3, 2025

(54) WEARABLE AND FLEXIBLE ELECTROCHEMICAL SWEAT SENSOR CONSISTING OF A POLYMER COMPOSITE MEMBRANE CONTAINING GRAPHENE

(71) Applicant: UNIVERSITA' DEGLI STUDI DI ROMA "LA SAPIENZA", Rome (IT)

(72) Inventors: Maria Sabrina Sarto, Rome (IT); Hossein Cheraghi Bidsorkhi, Rome (IT); Alessandro Giuseppe D'Aloia, Narni (IT); Alessio Tamburrano, Ciampino (IT); Lavanya Rani Ballam, Rome (IT)

(73) Assignee: UNIVERSITA' DEGLI STUDI DI ROMA "LA SAPIENZA", Rome (IT)

( * ) Notice: Subject to any disclaimer, the term of this patent is extended or adjusted under 35 U.S.C. 154(b) by 0 days.

(21) Appl. No.: 18/578,541

(22) PCT Filed: Jul. 15, 2022

(86) PCT No.: PCT/IB2022/056525
§ 371 (c)(1),
(2) Date: Jan. 11, 2024

(87) PCT Pub. No.: WO2023/002319
PCT Pub. Date: Jan. 26, 2023

(65) Prior Publication Data
US 2024/0293053 A1    Sep. 5, 2024

(30) Foreign Application Priority Data
Jul. 19, 2021    (IT) ........................ 102021000019073

(51) Int. Cl.
*A61B 5/145*    (2006.01)
*A61B 5/00*    (2006.01)
(Continued)

(52) U.S. Cl.
CPC ...... *A61B 5/14546* (2013.01); *A61B 5/14517* (2013.01); *A61B 5/1468* (2013.01);
(Continued)

(58) Field of Classification Search
CPC ............ A61B 5/14546; A61B 5/14517; A61B 5/1468; A61B 5/6801; A61B 2562/12; A61B 2562/164
See application file for complete search history.

(56) References Cited

U.S. PATENT DOCUMENTS 10,727,537 B2 * 7/2020 Stolyarov ............. H01M 4/485
10,923,760 B2 * 2/2021 Ho ........................ H01M 4/139
(Continued)

FOREIGN PATENT DOCUMENTS

WO           9400048 A1      1/1994

OTHER PUBLICATIONS

Bidsorkhi et al., Flexible Graphene Based Polymeric Electrodes for Low Energy Applications, 2020 IEEE 20th International Conference on Nanotechnology (IEEE-NANO), IEEE, Jul. 29, 2020, pp. 263-266, (submission pending).
(Continued)

*Primary Examiner* — Eric F Winakur
(74) *Attorney, Agent, or Firm* — NIXON & VANDERHYE

(57) ABSTRACT

A multi-composite electrochemical cell substantially consists of a thin polymer membrane including three different adjacent sectors, which are made of the same appropriately seamlessly modified polymer, incorporating in the polymer one or more conductive phases, or conductive fillers, such as graphene, metal, or a combination thereof. In the first sector the polymer material incorporates graphene nanoplatelets and acts as a cathode; in the second sector, interposed between the other two, the polymer material acts as an
(Continued)

insulating spacer; in the third sector the polymer material incorporates graphene nanoplatelets and a metal filler or immersed metal contact rheophore, with negative standard reduction potential, and acts as an anode; wherein the metal filler is in the form of dispersed powder or dispersed flakes, or of a thin sheet incorporated in the polymer.

12 Claims, 32 Drawing Sheets

(51) Int. Cl.
*A61B 5/1468* (2006.01)
*C01B 32/225* (2017.01)

(52) U.S. Cl.
CPC .......... *A61B 5/6801* (2013.01); *C01B 32/225* (2017.08); *A61B 2562/12* (2013.01); *A61B 2562/164* (2013.01); *C01P 2006/40* (2013.01)

(56) References Cited

U.S. PATENT DOCUMENTS

| 2015/0000118 A1* | 1/2015 | Zhao | H01M 4/1393 |
| | | | 29/623.5 |
| 2015/0027900 A1 | 1/2015 | Dryfe et al. | |

OTHER PUBLICATIONS

Bidsorkhi et al., Porous Graphene Based PVDF Aerogel Composite for Sweat Sensing Applications, 2018 IEEE 18th International Conference on Nanotechnology (IEEE-NANO), IEEE,, Jul. 23, 2018, pp. 1-4, (submission pending).
International Search Report for PCT/IB2022/056525 mailed Nov. 4, 2022, 4 pages.
Written Opinion of the ISA for PCT/IB2022/056525 mailed Nov. 4, 2022, 4 pages.

* cited by examiner

WEARABLE AND FLEXIBLE ELECTROCHEMICAL SWEAT SENSOR CONSISTING OF A POLYMER COMPOSITE MEMBRANE CONTAINING GRAPHENE

CROSS-REFERENCE TO RELATED APPLICATIONS

This application is the US national stage of PCT/IB2022/056525, filed Jul. 15, 2022 and designating the United States, which claims the priority of IT 102021000019073, filed Jul. 19, 2021. The entire contents of each foregoing application are incorporated herein by reference.

BACKGROUND OF THE INVENTION

Field of the Invention

The object of the present invention is an electrochemical cell consisting of a polymer composite material incorporating in said polymer one or more conductive phases (conductive filler) and usable in the presence of a saline solution adapted to close the circuit and generate a voltage at the heads of the aforementioned membrane.

Description of the Related Art

The development of wearable, manageable, reusable and easy-to-use sweat sensors even in everyday contexts is of primary importance in various markets and reference sectors, including the medical, home and hospital healthcare, and fitness fields.

Wearable sensors are arousing increasing interest for the multiple applications thereof, ranging from computerized healthcare to fitness, to worker safety.

In fact, the detection of physiological parameters, in real time and non-invasively, is essential for checking the physical and health status of patients, and more generally of people, who need continuous and prolonged monitoring, and is certainly very important for athletes and workers.

In this context, sweat sensors are becoming increasingly important, since sweat is relatively easy to remove and contains numerous biochemical information on people's physiological and health conditions.

Sweat is a biofluid which generally contains urea, lactate, glucose, and several electrolytes, including chloride and sodium ions.

These components can act as biomarkers for various diseases and are also useful for assessing the patient's electrolyte balance and hydration level.

The chloride ion is the electrolyte most present in sweat and can be useful for diagnosing diseases or states of physiological alteration due to, for example, dehydration or intensive exercise during both sports and during work activities.

For example, patients with cystic fibrosis generally have a variable sweat chloride ion concentration in a range between 60 mM and 150 mM; this range is much higher with respect to what is measurable in healthy individuals (10-40 mM).

Therefore, the development of effective, non-invasive and cost-effective wearable sweat sensors is a major and current technological challenge.

At the moment, the most accredited types of sensors are chemical titration, potentiometric and conductivity devices.

The first involve the use of analytical chemical techniques, are precise but require expert personnel to perform the analysis and are difficult to apply in everyday contexts.

Conversely, the potentiometric and conductivity sensors offer simplicity and ease of detection, making the technique attractive for daily and real-time applications.

Potentiometric sensors measure the electrochemical potential of sweat with respect to that of a reference electrode placed in contact with the skin, and therefore need to be installed on the person's skin; they make use of complex electrodes and a salt bridge and the electrodes are generally expensive, especially the one of reference.

However, the reliability thereof is affected by the time of use since the salt concentration of the sweat and the salts present on the skin can change the concentration of the reference solutions, altering the sensor response.

Basically, for all these reasons, there are no large-scale potentiometric sweat sensors on the market to date which can be used by anyone and in any daily context.

Conductivity sensors measure the change in the electrical conductivity of the skin due to the presence of sweat.

In this case, these are also skin sensors which require highly performing electrodes in contact with the skin and need power supply.

Moreover, the response thereof can be distorted by particular conditions, such as the rapid evaporation of sweat and the presence of various kinds of salts on the epidermis which alter the salt concentration of sweat and consequently the sensor response.

It is therefore of crucial interest to develop a technology for the creation of low-cost sweat sensors, lacking electrodes in contact with the skin (and therefore not cutaneous) but wearable as they are integrated into clothes or accessories, and thus flexible, washable and low-cost.

The types of sensors used today include those of a voltametric type or those which use electrochemical impedance spectroscopy.

This technique is very useful for detecting heavy metals, drugs and hormones in sweat but requires the intervention of technical personnel for the data processing and analysis.

Other sensors currently available are optical and colorimetric ones; they contain reagents that undergo visible color changes after being exposed to sweat or the analyte of interest contained therein. These techniques are not easy to use, as they require a sweat collection step and the response thereof can be difficult and not unambiguous.

For example, the idea of incorporating such sensors into bracelets or elastic bands is very attractive, so that they can be worn comfortably and without the slightest obstacle to movement, especially during motor activity. The patch format is instead preferred for medical purposes, given the excellent adhesion thereof to the skin. The most studied substrates consist of soft polymer substances, sometimes placed on temporary tattoos, or hybrid systems which combine polymer materials with traditional silicon integrated circuits.

Currently, the sweat sensors most studied for "wearable" applications are of the potentiometric type; as already mentioned, they measure the difference in electrochemical potential between a working electrode and a reference electrode (RE) when they are in contact with a saline solution such as sweat.

The measured voltage difference is indicative of the ion concentration in the solution under consideration. In order to monitor a single ionic species, the working electrode is often coated with a membrane which is selective to different ionic species, so as to obtain an Ion-Selective Electrode (ISE).

However, these sensors have some disadvantages, including cost and a non-immediate response.

The following are the main patents which address the identification of sweat biomarkers for fitness and health monitoring.

As will be better seen below, most such patents employ RE and at least one ISE for monitoring ion concentration; furthermore, unlike the present invention, the patents listed do not consider or suggest the use of any graphene-based polyvinylidene fluoride (PVDF) polymer composite film for sweat detection applications.

Patent application WO2017/192836 A1 "A potentiometric measurement of sweat sensor-related applications" describes a potentiometric sensor adapted to measure the concentration of chloride ions in sweat for the diagnosis of cystic fibrosis; said potentiometric sensor comprising a reference electrode RE, a working electrode and salt bridge with a selective ionic polymer, all incorporated in polydimethylsiloxane (PDMS). The reference electrode consists of Ag/AgCl and is covered by a hydrogel containing the reference solution. Once sweat is generated, the ions of the sweat form an ionic circuit between the RE and the working electrode. The measured difference of potential between these electrodes is proportional to the concentration of ions in the sweat. However, this patent has some disadvantages: the manufacturing process is long and complicated, the required electrodes are expensive and not least the transport of ions between the reference solution and the test solution is often slow; this implies that the sensor response is not immediate and that the device shows reliable performance only for 12 hours since the hydrogel can dry out, altering the RE reference solution. In fact, if altered, the reference solution contained in the hydrogel could induce interference due to the potential established between the internal reference solution and the external sweat chloride ions during the measurements.

Patent application US2015/0126834 A1 "Wearable Electrochemical sensors", describes a device incorporated in temporary epidermal tattoos containing different electrochemical biosensors with different configurations; the detection electrodes are screen-printed on coated paper substrates, and the purpose is to detect different biomarkers in sweat. For example, a potentiometric sensor consists of an ISE with a layer of polyaniline (PANI) as insulator followed by screen-printed reference electrodes and carbon. However, the temporary epidermal tattoos, such as those indicated in this patent, are expensive and non-reusable; they require complicated manufacturing processes and a modified Ag/AgCl reference electrode. Electrochemical analysis for biomarker detection can also implicate long processing times.

Patent application US2018/0263539 A1 "Wearable sensor array for insitu body fluid analysis" describes a wearable smart bracelet with sensor array wirelessly connected to flexible circuitry for monitoring skin temperature and specific biomarkers. This device consists of electrodes coated with membranes selective to sodium and chloride ions and electrodes sensitive to lactate and glucose. The reference electrode is coated in PVB, is based on Ag/AgCl and the whole is inserted into a polyethylene terephthalate (PET) substrate. However, for the device according to such a patent application, an Ag/AgCl reference electrode adapted for skin applications together with several components and an electrical supply is necessary; it also has a considerable cost, is not washable and therefore is not suitable for workers such as those in construction and agriculture.

Patent application US2018/0070870 A1 "Autonomous sweat extraction and analysis using a fully integrated wearable platform" describes a device consisting of electrodes sensitive to sodium and chloride ions and an Ag/AgCl type reference electrode coated in polyvinyl butyral (PVB) with all the detection elements integrated in a bracelet and controlled by a smartphone app. In order to extract the sweat, a hydrogel containing a pilocarpine-type drug is used. This device requires a power source, is expensive because it requires a long manufacturing process and the contamination of the sweat ions through the administration of pilocarpine-based drugs for sweat induction can affect the outcome.

Patent U.S. Pat. No. 9,603,560 B2 "Flexible electrode for detecting changes in temp hum and sodium ion concentration in sweat" describes a method for manufacturing a flexible sensor to be kept in contact with the skin; in this case the sensor consists of a three-layer structure for detecting salt components such as sodium and chloride ions in sweat biofluid. The first layer consists of a non-conductive polyamide-Nylon-6 substrate, the intermediate layer is a nanocomposite containing carbon/graphene/multi-walled carbon nanotube (MWCNT), while the upper layer consists of a calixarene-functionalized polymer for detecting the salt components of sweat in order to determine the concentrations of sodium $Na^+$ and chloride $Cl^-$ ions. Other functionalized polymers (such as polypyrrole-PPy) are used for detecting moisture and temperature. The disadvantages related to the sensor according to the aforementioned patent relate to the rather complex manufacturing process, and not immediate use, so as to require experienced professionals; furthermore, measurements which require additional time and functionalization processes on the top of the graphene layer with ion-selective layers are necessary. Finally, the patent does not propose innovative electrodes but uses commercial electrodes, which are not reusable and not compatible with the conduct of daily activities.

Patent application WO1994/000048 A1-"Device with sensors to detect a value depending on the chloride and sodium concentration" describes a device for measuring the conductivity of solutions containing chloride and sodium ions using a polymer substrate containing electrodes sensitive to these ions, coated with PVB, the main application of which is the early diagnosis of cystic fibrosis. However, the production process is complicated; it requires reference and ion-selective electrodes for detecting the ions, and this makes the system more complex; further, power supply is necessary and the sensor is not reusable, but suitable for single use.

Patent application US2017/0172484 A1 "Combinatorial sensing of sweat biomarkers using potentiometric and impedance measurements" describes a sensor for measuring the concentration of different biomarkers contained in sweat using multiple ion-selective electrodes (ISE) placed on the same substrate. This patent uses commercially available sensors for ion detection. Each ISE detects a specific analyte, so there is a possibility of errors in the voltage measurements due to possible interference with other ions present in sweat, such as $K^+$ with Nat. Moreover, the data analysis is not easy.

Patent application US2019/0008448 A1 "Sweat Electrolyte loss monitoring devices" describes several methods for incorporating sweat using a suspension based on an aqueous polymer matrix (e.g., polyvinylpyrrolidone (PVP), collagen, polyalkylene glycol (PAG) gelatin) and a thixotropic compound (e.g., fumed silica) containing a salt of the target analyte. The detection device consists of ion-selective electrodes, reference electrodes and an ion exchange membrane. The whole is contained in a wearable device which can be used to monitor the loss of sweat electrolytes during exercise. The suspension in the reference electrodes and in the ion-selective electrodes serves as a salt suspension structure which allows the exchange of ions between the electrode and the sweat sample. The noteworthy disadvantages relating to this device include: the manufacture of the device is long and difficult, different materials are needed in the suspensions as well as expensive electrodes for monitoring the electrolyte concentration, together with the ion exchange ports, the use of hydrogel suspension material leads to the formation of bubbles, and requires a watertight seal in the sweat detection device.

Patent application US2019/0110722 A1 "Apparatus for noninvasive sensing of biomarkers in human sweat" relates to patches and other wearable devices comprising biofluid detection devices for in situ, continuous and noninvasive monitoring of biomarkers (e.g., proteins, hormones, ions) in biofluids. However, this device is expensive and requires complicated manufacturing steps, as well as electrodes sensitive to different ionic species. Semiconductor materials are needed to make it, and the functionalization of the gate materials is required. Finally, there is no provision for multiple and lasting use of the sensitive elements.

Patent application US2018/0344222 A1 "Sweat monitoring and drug delivery" describes a skin patch for the administration of a medicament together with the detection of sweat; the sensitive elements present on the patch allow detecting information on the dosage of the drug, measuring the concentration of specific analytes or metabolites present in the sweat itself. However, this system is limited to medical and hospital applications, requires a complex design and manufacture, ion-selective reference electrodes and expensive techniques for sweat monitoring.

U.S. Pat. No. 10,136,831 B2 "Sweat sensing with chronological assurance" describes a platform consisting of several commercial detection elements capable of detecting different sweat biomarkers and determining sweat quantities such as sweat sampling rate. The sensitive elements in the patent lack novelty, and require ion-selective electrodes, Ag/AgCl reference electrodes for the detection of ions in sweat; the platform presented is expensive, requires a non-negligible processing time and sees the main application thereof in the medical or hospital field.

Some of the major scientific publications addressing the identification of sweat biomarkers are presented below.

As will be seen, even in this case most of the articles employ RE and at least one ISE for monitoring the ion concentration; furthermore, no article considers/suggests the use of any multi-composite polymer film similar to that which is the object of the present invention.

Serdar Dinc et al. "Improved sensing response of nanostructured CuO thin films towards sweat rate monitoring: Effect of Cr doping" (2020): this work addresses the effect of chromium doping copper oxide (CuO) structures on the main physical properties and on the ability to detect the hydration level of thin films synthesized with the "Successive Ionic Layer Adsorption and Reaction" (SILAR) technique. The tests were performed by applying a difference of potential of 5V on the surface of the manufactured film and measuring the reported direct current values by depositing 10 μl drops of sweat or a saline solution on different chromium-doped CuO films. However, the required response time is very high (about one minute) and the measured current is not as stable over time. Furthermore, the manufacture of chromium-doped CuO metal oxide nanostructures is difficult and the sensor requires an external power supply for the measurement.

Marc Parrilla, et al., "Wearable Potentiometric Potentiometric ion patch for on body electrolyte monitoring in sweat towards a validation strategy to ensure physiological relevance", (2019): in this work, the electrodes are circular in shape and prepared with carbon-based ink and are connected by a coil made with silver-based ink. The whole is made on a stretchy polyurethane fabric, with the screen-printing technique. Subsequently, the electrodes were modified first by depositing a layer of multiple-walled carbon nanotubes (MWCNTs) and then adding a selective membrane to select some ions such as Cl−, K+, Na+. Although the screen-printing technique is very widespread, the manufacture of the sensor is not simple and requires sophisticated equipment for electrode printing (SPR-45 automatic printer SMT stencil SMT, DDM, Novastar Inc. USA). An expensive commercial Ag/AgCl reference electrode is also required for the measurements. Moreover, the voltage response at the different NaCl concentrations is very similar to that detected in the present invention, with the difference which—advantageously—the present invention does not require any reference electrodes.

Dong-Hoon Choi et al., "A wearable potentiometric sensor with integrated salt bridge for sweat chloride measurement", (2017): in this work, the potentiometric sensor is incorporated in a polyethylene terephthalate (PET) film made adherent to the skin by means of an adhesive bandage. The sensor consists of an Ag/AgCl reference electrode and working electrodes located on opposite sides of the PET film and connected to the reference electrode by means of a salt bridge. The aim is to monitor, by means of a complicated experimental setup, the concentration of chloride ions in sweat for medical applications, such as the diagnosis of cystic fibrosis, and in the field of fitness, such as the detection of dehydration states due to intensive exercise. However, a manufacturing process which is not simple with long processing steps is described, expensive reference electrodes are required whose solutions are contained in special hydrogels. And it is precisely the latter which are a critical issue in the medium to long term, as the hydrogel can dry over time, changing the concentration of salts in the reference solution.

Redondo-Cubero, et al., "Zinc nitride thin films: basic properties and applications", (2017); in this work, zinc nitride thin films are deposited by sputtering using a Zn target at temperatures below 250° C. on flexible substrates placed in contact with the skin. Metal contacts are deposited on the thin film of Zn3N2 thus manufactured, through which the difference in potential during training or sleep is measured, a difference which varies depending on the amount and quality of sweat. It should be noted that the manufacturing process shown requires sophisticated equipment and complicated procedures and an external voltage source is needed.

Marc Parrilla, et al. "A textile-based stretchable Multi-Ion potentiometric sensor", (2016): in this work, a potentiometric sensor made by screen-printing technique on a polyurethane fabric is proposed. A reference electrode and ink-covered carbon electrodes based on multiple-walled carbon nanotubes (MWCNTs) and selective ion membranes are used. The manufacturing process presented is more difficult than that object of the present invention and, although an expensive reference electrode is used, the voltage response to the different NaCl concentrations is very similar to that detected in the present invention.

SUMMARY OF THE INVENTION

The main object of the present invention is to overcome the limits of the prior art by providing an electrochemical cell and a related production process, usable as a wearable sweat sensor or for low energy applications for the generation of voltage and thus of electricity.

The proposed solution according to the present invention, substantially consists of a multi-composite electrochemical cell which is easy to use, low-cost, usable several times and washable, consisting of a thin polymer membrane which, once in contact with sweat, produces a voltage signal the intensity of which depends on the salt concentration of the sweat itself; said voltage signal can be used as both a parameter for interpreting the salt content data of said solution, and for low energy applications.

BRIEF DESCRIPTION OF THE DRAWINGS

A better understanding of the invention will be obtained from the following detailed description and with reference to the accompanying figures, showing, by way of a non-limiting example, a preferred embodiment and a variant thereof.

In the drawings:

FIG. 4a shows the dissolution of the PVDF;

FIG. 4b shows the sonication of the mixtures;

FIG. 4c shows the casting of the mixtures;

FIG. 4d shows the curing in the oven;

FIG. 4e shows the final product.

FIG. 22a shows the surface of the sector consisting of PVDF-GNP;

FIG. 22b shows high-resolution detail which highlights the excellent integration of GNP in the polymer;

FIG. 22c shows the surface of the sector which incorporates the aluminum sheet on the side coated with only PVDF (C);

FIG. 22*d* shows the surface of the sector which incorporates the aluminum sheet on the PVDF-GNP nanocomposite coated side.

FIG. 24*a*: aluminum atom mapping;

FIG. 24*b*: fluorine atom mapping.

DETAILED DESCRIPTION

The invention relates to a multi-composite electrochemical cell, and a related production process, consisting of a thin polymer membrane provided with 3 different adjacent sectors and made, seamlessly, with the same polymer suitably modified, incorporating in some parts of said polymer one or more conductive phases (conductive filler) such as graphene, metal or a combination of graphene and metal.

Figure 1:
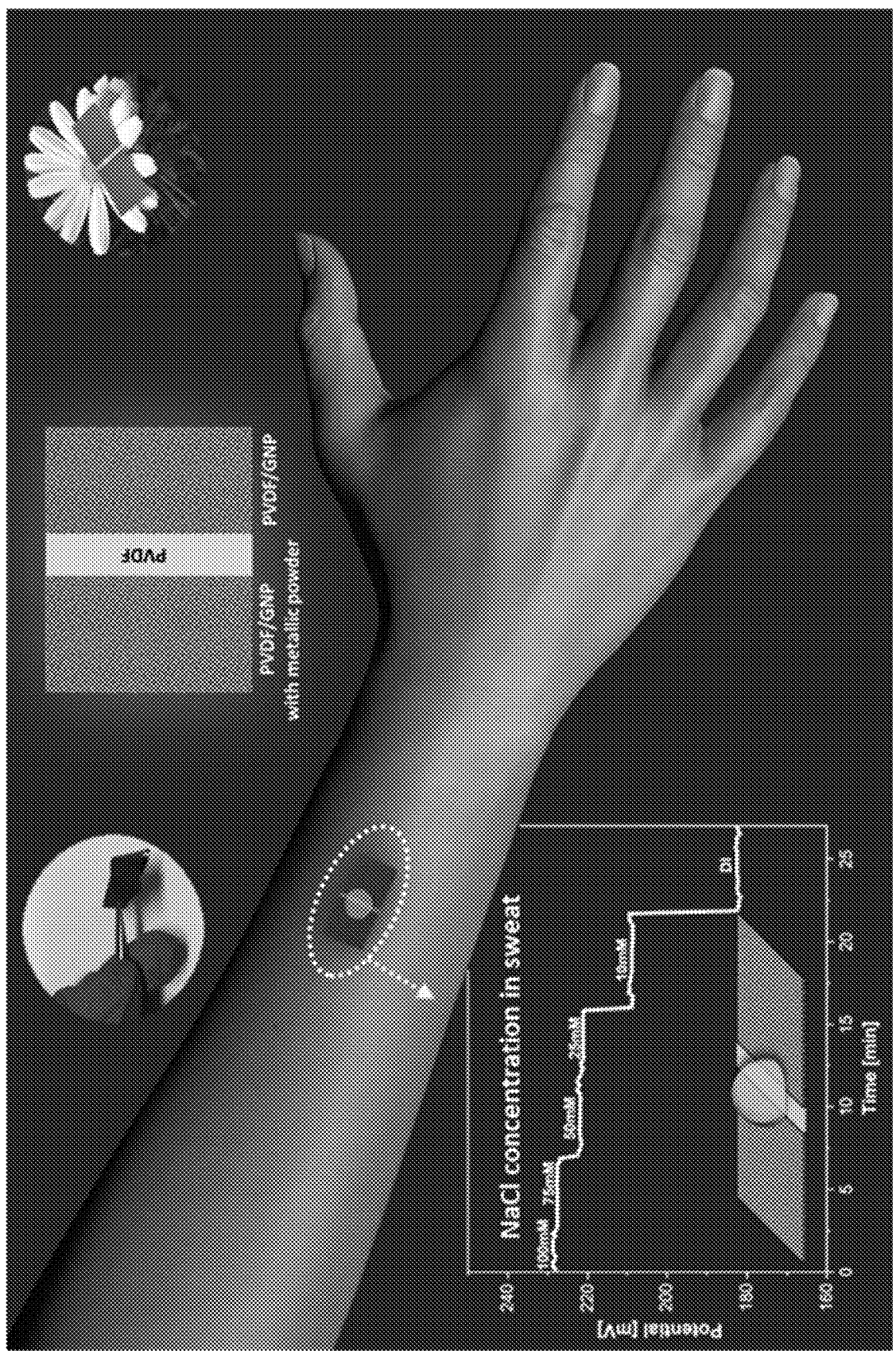
FIG. 1 shows a diagram of the electrochemical cell, object of the present invention, used as an electrochemical sweat sensor and consisting of a membrane in polymer composite material containing graphene.

FIG. 1 shows the simplified diagram of said electrochemical cell; as can be seen from such a figure, the cell does not require electrical power supply for signal detection since—advantageously—it behaves as an active component in the presence of a conductive solution such as sweat.

According to the invention, the membrane forming the electrochemical cell incorporates three sectors with different composition and functionality, indicated below with S1, S2 and S3 and shown in FIG. 2 (*a*):

The first sector (S1) is made of polymer composite material in which graphene nanoplatelets are incorporated and acts as a cathode;

The second sector (S2) is made of polymer material and acts as an insulating spacer between the other two sectors between which it is interposed;

The third sector (S3) is made of polymer composite material, graphene nanoplatelets and a metal with negative standard reduction potential, incorporated in the form of dispersed powder or flakes, or of thin sheet incorporated in the polymer, or of contact immersed rheophore; said sector S3 acts as an anode.

The resulting membrane is self-standing, lightweight, flexible and maneuverable.

Furthermore, according to the invention, the conductive filler is chosen so that the two lateral sectors of the polymer membrane are characterized by a different electrochemical potential and thus act, in the presence of an electrolyte, as electrodes of the electrochemical cell: in the presence of a saline solution, such as sweat, the circuit closes generating a voltage and creating, in fact, the sensor.

In fact, in the first sector (S1) of the membrane consisting of polymer loaded with graphene, if placed in contact with a conductive solution such as sweat, reduction reactions occur, while in the third sector (S3) made by adding a third metal phase, also in the form of contact immersed rheophore (with negative standard reduction potential), oxidation reactions occur.

Consequently, when both conductive sectors (S1, S3) of the membrane are brought into electrical contact with each other by means of even small amounts of conductive solution, such as sweat, an electrochemically generated voltage signal is obtained which is dependent on the concentration of the ions dispersed in said conductive solution which closes the circuit.

Therefore, considering the use of said voltage generated for the interpretation of data related to the salt content in the electrolytic solution, and thus the use of the electrochemical cell as a sensor, it is immediately noted that the type of sensor proposed is completely different from that of the potentiometric type, as it generates a voltage signal by electrochemical means without having to resort to complex printed electrodes, reference electrodes, skin contact electrodes or salt bridges, and without the need for electrical power supply.

For the purposes of making the device according to the present invention, the following are therefore of fundamental importance:

(i) the choice of the polymer, which must have the function of a binder between electrodes and a current collector and which must also ensure a high sensitivity in the sensor response, facilitating the exchange of charge;

(ii) the choice of conductive phases to be dispersed in the polymer to make the two electrodes;

(iii) the production process of the polymer nanocomposite and the sensor, necessary to ensure high sensitivity and accuracy in the response.

With regard to the first two aspects, it is important to emphasize that the development of conductive polymer matrix nanocomposites has seen extensive progress in the last decade, with applications ranging from electromagnetic shielding, to sensors, to flexible electronics, to devices for the storage and generation of energy by electrochemical means.

In general, polymer materials typically have a limited ability to conduct electric current, but such a property can be improved by virtue of the addition to the polymer of an appropriate conductive phase consisting of particles of micro or nanometric size, such as carbon and, more specifically, graphene nanostructures.

The invention includes the use of polyvinylidene fluoride (PVDF) as a polymer for the excellent chemical and mechanical properties thereof and for the workability thereof.

In general, polyvinylidene fluoride (PVDF) is a highly non-reactive thermoplastic fluoropolymer and typically used in applications which require maximum purity and resistance to solvents, acids and hydrocarbons.

The uses of this type of polymer are very diverse, in fact it is used in many different areas, such as in semiconductors, in the pharmaceutical industry, in sensors.

Furthermore, being chemically inert and electrochemically stable, PVDF is being widely used in next-generation batteries, in which it can be used as a binder in electrodes; in fact, in lithium batteries, the binder plays a key role as it acts as an effective dispersing agent to connect the electrode species together and thus make them permanently adhere to the current collector.

In particular, PVDF is one of the most common binders used for the cathode in lithium-ion batteries; this is due to its superior electrochemical stability and its excellent adhesion properties between current collector and electrode membrane, a characteristic which ensures a longer cycle duration and a higher energy density.

Further, the polar functional groups of PVDF produce less internal energy.

Lastly, PVDF is a biocompatible polymer with a very low microbiological attachment.

Among the most common carbon-based fillers, graphene nanoplatelets (GNP) have excellent electrical properties, are low cost, easy to use as a filler within a polymer matrix, by virtue of the two-dimensional geometry thereof, and have been the subject of numerous studies.

Advantageously, the high aspect ratio of graphene nanoplatelets (GNP), characterized by nanometric thicknesses and lateral dimensions of the order of microns or tens of microns, allows controlling the electrical properties of the final composite, even with relatively low filler concentrations.

When the conductive solution, such as sweat, comes into contact with the surface of the aforesaid membrane, the sensor is activated as an electrolytic cell, producing a voltage signal detectable between anode and cathode and proportional to the salt content in the electrolyte.

According to the invention, the three-sector PVDF membrane is continuous, flexible and is obtained through a single production process easily exportable on an industrial scale; the cathode electrode (S1) is made of PVDF loaded with graphene nanoplatelets (GNP) while the anode (S3) consists of a 3-phase composite material containing PVDF, GNP and a metal (also in the form of a contact immersed rheophore) with negative standard reduction potential. Lastly, the intermediate sector (S2) with spacer function is in PVDF.

Figure 2A:
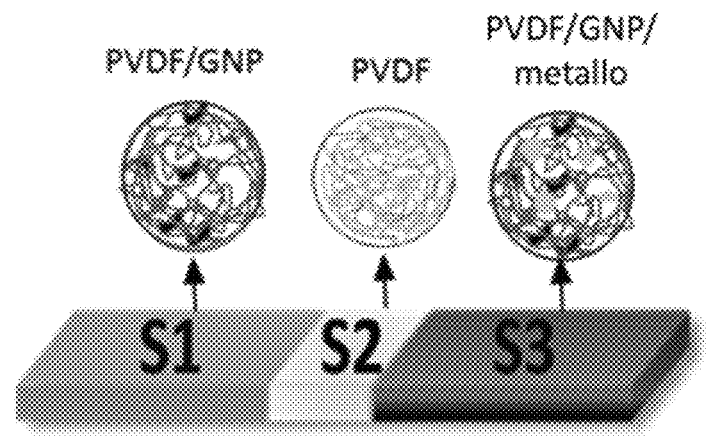
FIG. 2a shows a constituent diagram of the electrochemical cell comprising the three sectors S1, S2 and S3.
Figure 2B:
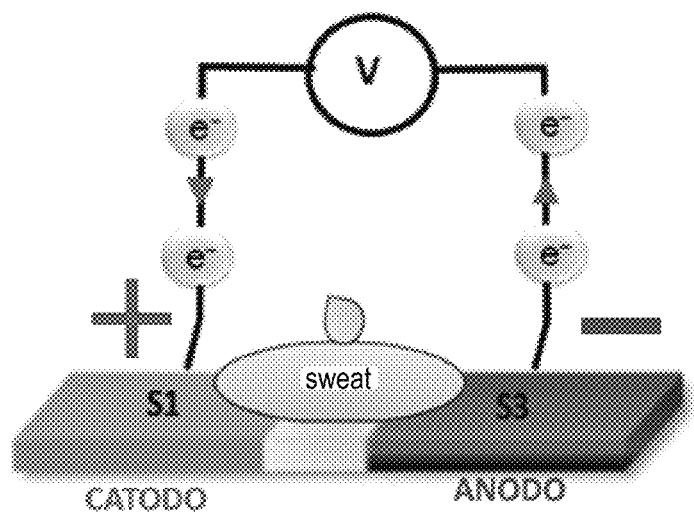
FIG. 2b shows the operating principle of said electrochemical cell.

The operating principle of the sensor is diagrammed in FIG. 2(b); in particular, the first sector (S1) of the membrane consisting of PVDF and GNP, if in contact with a conductive solution, is the site of oxygen reduction reactions present in the solution, while the third sector (S3) with the addition of further metal elements is the site of oxidation reactions thereof.

Consequently, when both sectors are in contact with even small amounts of conductive solution, such as (but not limited to) sweat, electrons pass from the third sector (S3), the oxidation reaction site, to the first sector (S1), the reduction reaction site.

Consequently, the sector (S3) acts as an anode and thus assumes a negative polarity while the sector (S1) acts as a cathode and thus assumes a positive polarity.

Therefore, in such a situation, there is an electrochemically generated voltage signal the intensity of which depends on the ion concentration in the conductive solution (such as sweat or other saline solution), which simultaneously touches both sectors (S1 and S3) which act as cathode and anode and thus acts as an electrolyte solution.

The high sensitivity of the sensor according to the present invention, even for small amounts of electrolyte solution, is closely linked to the optimal integration of graphene in the PVDF polymer matrix, as well as to the dispersion uniformity of the metal powders within the third sector (S3).

Figure 2C:
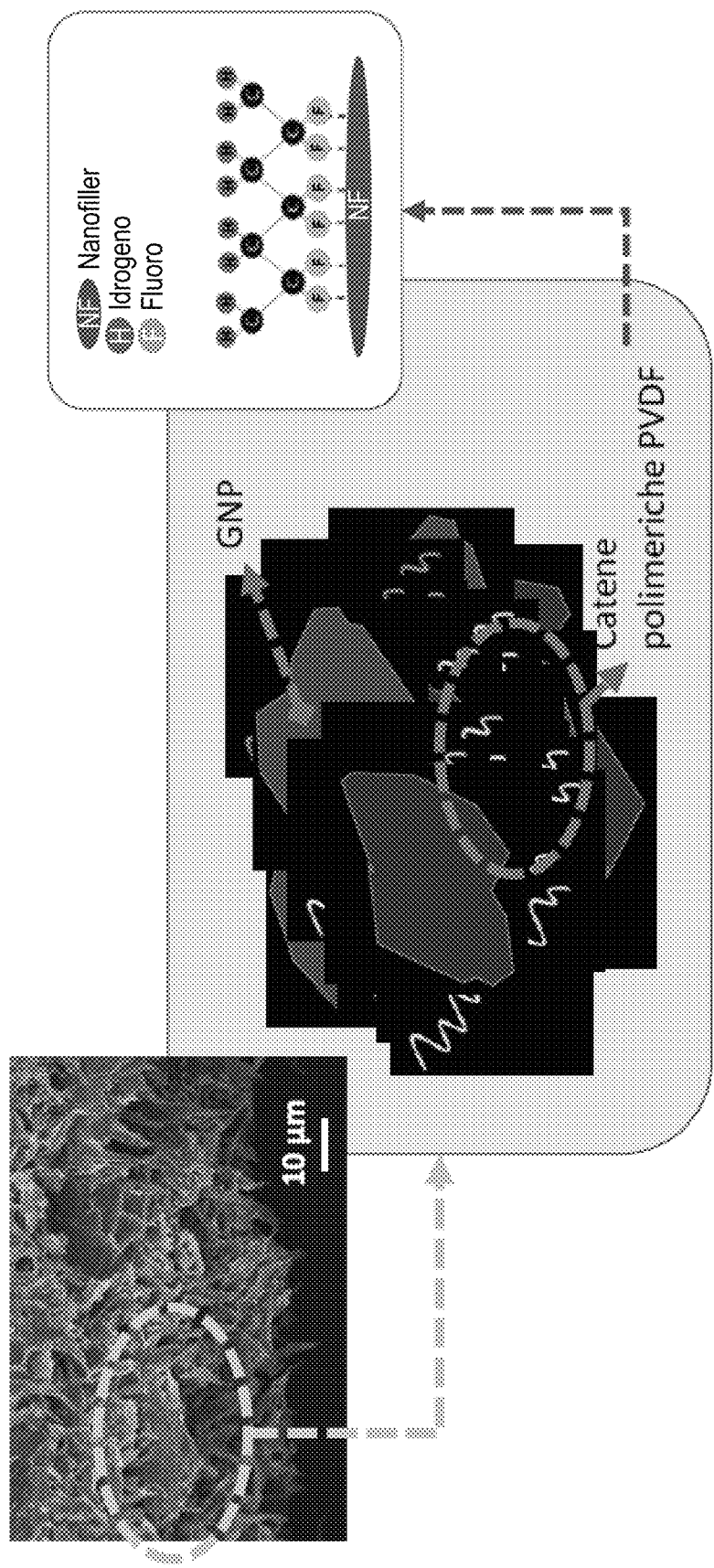
FIG. 2c shows the alignment effect of the PVDF polymer chains induced by the presence of the nanofiller.
Figure 3:
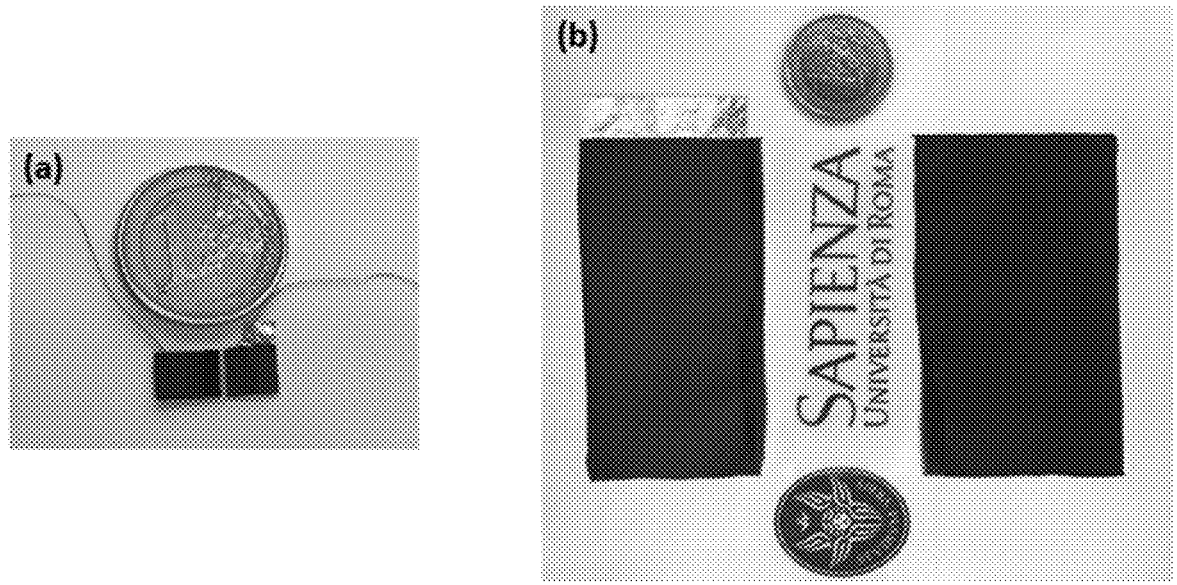
FIG. 3a shows a PVDF polymer membrane electrochemical cell, loaded with GNP on the sides and aluminum elements usable as a sweat sensor.
FIG. 3b shows a PVDF polymer membrane electrochemical cell, loaded with GNP on the sides and aluminum elements usable for low energy generation applications.

Said dispersion is obtainable by virtue of the specific production process, also the object of the present invention, which determines the alignment of the PVDF polymer chains (as shown in FIG. 2c), enhancing the electrochemical properties of the electrodes (S1, S3) thus made, also by virtue of the electrostatic interaction effect between the nanofiller and the fluorine group of the PVDF.

Specifically, the creation of the polymer membrane object of the present invention requires the use of the following reagents, chemical elements and products:
polyvinylidene fluoride (PVDF)
N,N-dimethylformamide (DMF),
metal powders, sheets or filaments (for example, Nickel and Aluminum), even in the form of contact immersed rheophores,
graphite intercalation compound (GIC).

Worm-like exfoliated graphite, or WEG, is produced by the thermal expansion of graphite intercalation compounds (GIC). In summary, the GICs are subjected to a thermal shock at a temperature above 1000° C. for a time between 4 and 8 seconds, causing a volume increase by about 200 times and the complete reduction.

The polyvinylidene fluoride PVDF film is first dissolved in N,N-dimethylformamide (DMF) by magnetic stirring, for a time period to a few hours (30 min to 4 hours), at a controlled temperature between 55° C. and 75° C., by way of non-limiting example at a temperature of 65° C. for 2 hours.

The PVDF and DMF solution thus obtained is partitioned into two beakers and worm-like exfoliated graphite (WEG) is added to the first beaker, prepared as previously indicated.

The resulting compound is homogenized by sonication, using an ultrasonic processor set with a pulsed cycle (typically 1 sec on and 1 sec off) and for an execution time of at least fifteen minutes, thus ensuring the exfoliation of the WEGs and obtaining a GNP suspension.

This step is particularly important, as it ensures an optimal dispersion and integration of the GNP in the polymer matrix, determining the excellent electrical and mechanical properties of the final compound by virtue of the orientation effect of the polymer chains caused by the electrostatic interaction with the GNPs.

After the sonication, there are two distinct mixtures: one consisting of PVDF+DMF only, the other of PVDF+DMF loaded with GNP.

Part of the mixture of PVDF+DMF and GNP is added with commercial metal powders or metal flakes, mixed by (mechanical or magnetic) stirring and/or ultrasonic bath, depending on the metal powders chosen or contact immersed metal rheophores.

Three mixtures are thus obtained: one consisting of PVDF+DMF only, another consisting of PVDF+DMF with GNP, the last consisting of PVDF+DMF, GNP and metal powders.

Subsequently, the three mixtures are cast on a mask appropriately provided, as described in the attached examples.

Figure 4:
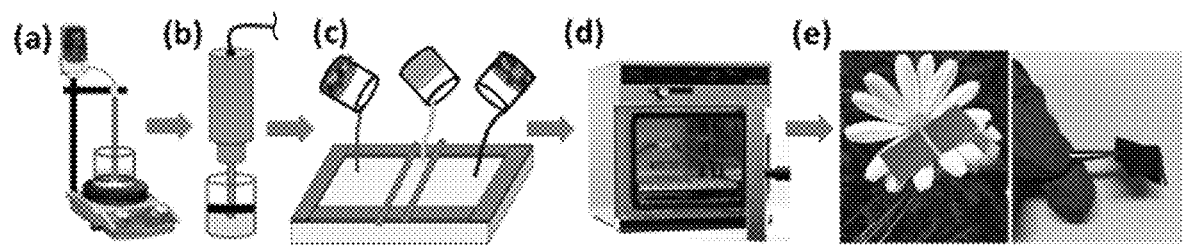
FIGS. 4a, 4b, 4c, 4d and 4e show the manufacturing process of the electrochemical cell consisting of the PVDF polymer matrix hybrid film, partially loaded with GNP and containing metal elements according to the invention where.

Finally, the mask with the cast mixtures is placed in the oven at 160° C. for a period between 1 and 6 hours. The process is diagrammatically shown in FIG. 4.

As already mentioned, the electrochemical cell produced according to the invention can have various application fields ranging from the use of the voltage generated as a vector for interpreting data concerning the electrolytic solution which comes into contact with the electrolytic cell itself, or even the use of said generated voltage for low energy applications.

Therefore, considering the application as a sensor, the invention allows an easy and immediate detection of the presence of sweat by electrochemical means, without the use of contact skin electrodes, or sweat collection elements, or electrodes with complex geometry, or reference electrodes with related salt bridge, allowing an easy measurement of the salt concentration in the sweat itself, all without the need for electrical power supply.

The detection of sweat and the measurement of the ion concentration in the sensor which is described allow monitoring physiological parameters for medical or sports purposes, the early diagnosis of diseases, the prevention of dehydration states and so on.

Advantageously, the invention—unlike most of the sensors currently available on the market, those patented and those under study which are not very easy to handle, difficult to use in everyday contexts and often require the use of specialized personnel for data analysis—is wearable, comfortable and easy to use, low-cost, usable several times and washable.

Furthermore, many of the known sensors make use of reference or contact electrodes, even expensive.

In summary, the present invention is innovative and original with respect to the background art in that:
  It is low-cost: it does not require the use of expensive reference electrodes
  It can be made with a simple process which leads to the production of a single polymer membrane with 3 continuous sectors
  It is easy to use and adaptable to various needs
  It is flexible, wearable, washable, reusable
  It does not require any external power supply because it is a device which feeds itself electrochemically in the presence of sweat or other conductive solution
  It is highly sensitive to small variations in electrolyte concentration by virtue of the presence of graphene integrated in the PVDF matrix
  It is biocompatible and has low bacterial proliferation
  It is chemically resistant
  It is designed to allow easy monitoring of electrolyte concentration with immediate signal response to changes in ion concentration (such as K+, Na+, Cl).

In order to demonstrate the feasibility and functionality of the object of the present invention, several sensors have been made at the prototype level so as to evaluate the effect of different anodic configurations. The operation thereof has been demonstrated by various experimental tests adapted to simulate different operating conditions and by applying conductive solutions consisting of saline solutions and/or synthetic sweat containing different amounts of NaCl.

From the experiments it has surprisingly been demonstrated that the 3-sector membrane described above can also be used to make an electrochemical cell for low energy applications. In particular, by way of explanation, two prototypes (or samples) of three-sector polymer membrane have been made, characterized and studied. The first sample measuring 1 cm×2.1 cm was tested as a sweat sensor; the second sample measuring 5 cm×9 cm was immersed in saline solution and tested as an electrolytic cell for low energy applications.

Example 1—Sweat Sensor Made of PVDF, GNP and Nickel Microparticles

By way of explanation, a sweat sensor such as that shown in FIG. 2 (*a*). In particular, nickel powders were used and the PVDF was loaded with an amount of GNP equal to 11% by weight of the PVDF.

Figure 5:
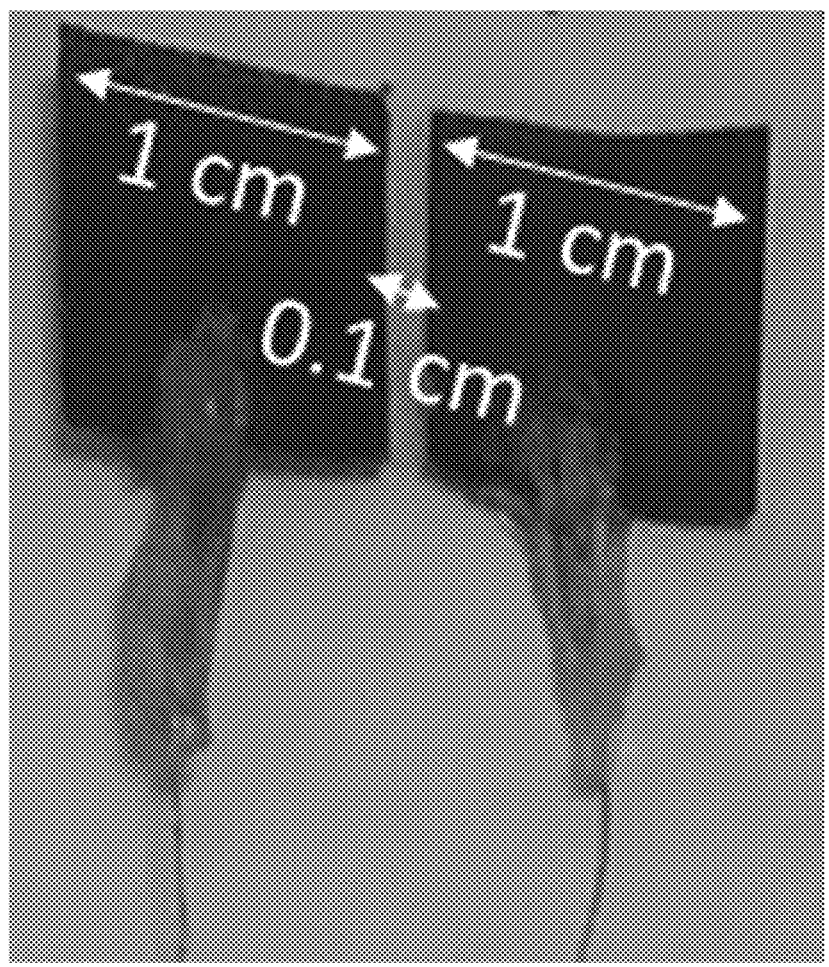
FIG. 5 shows a photograph of the invention in polymer multi-composite material with PVDF polymer matrix, loaded with GNP on the sides and Nickel micro-particles of Example 1.
Figure 6A:
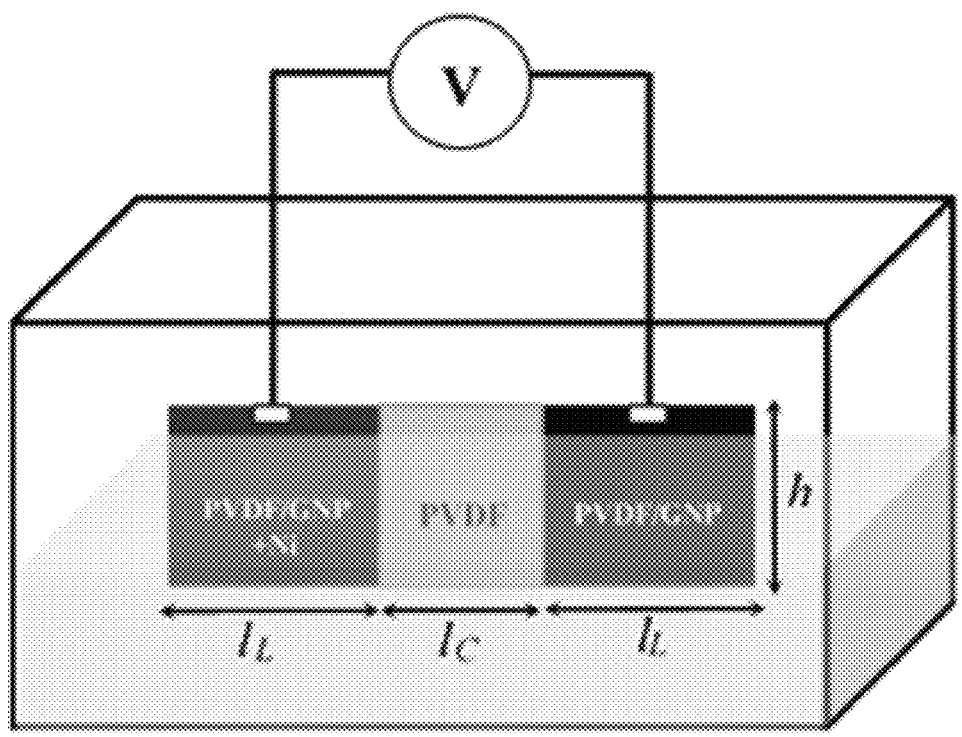
FIG. 6a shows a diagrammatic image of the immersion test of Example 2.
Figure 6B:
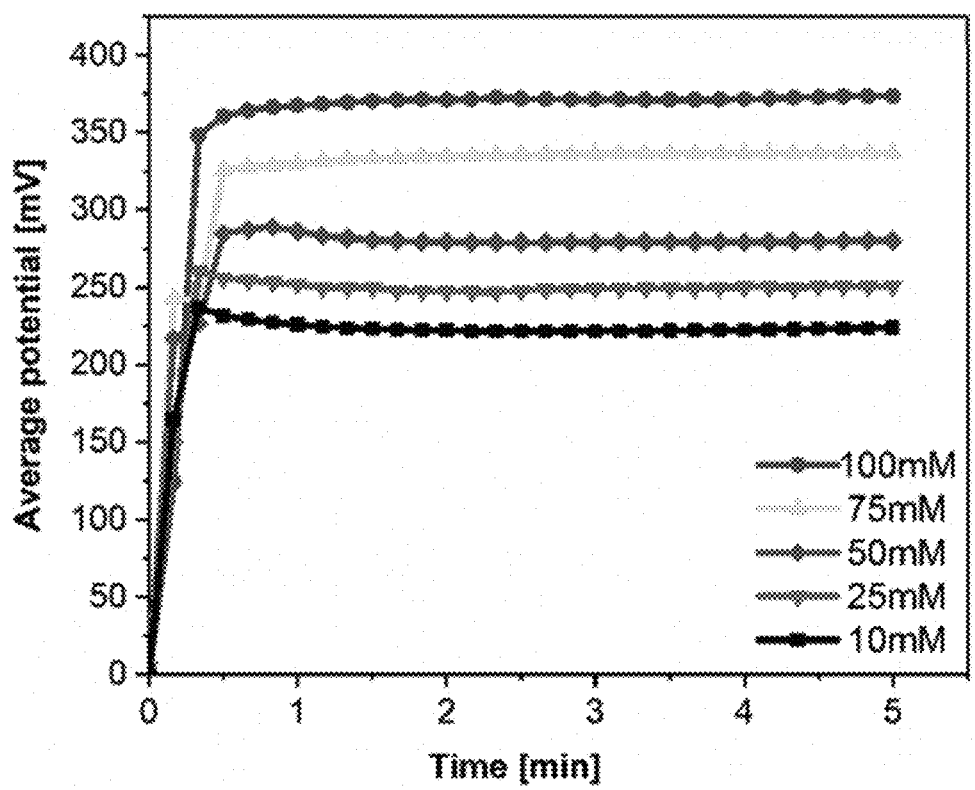
FIG. 6b shows the trend of the voltage signal generated as a function of time for different NaCl concentrations of Example 2.
Figure 6C:
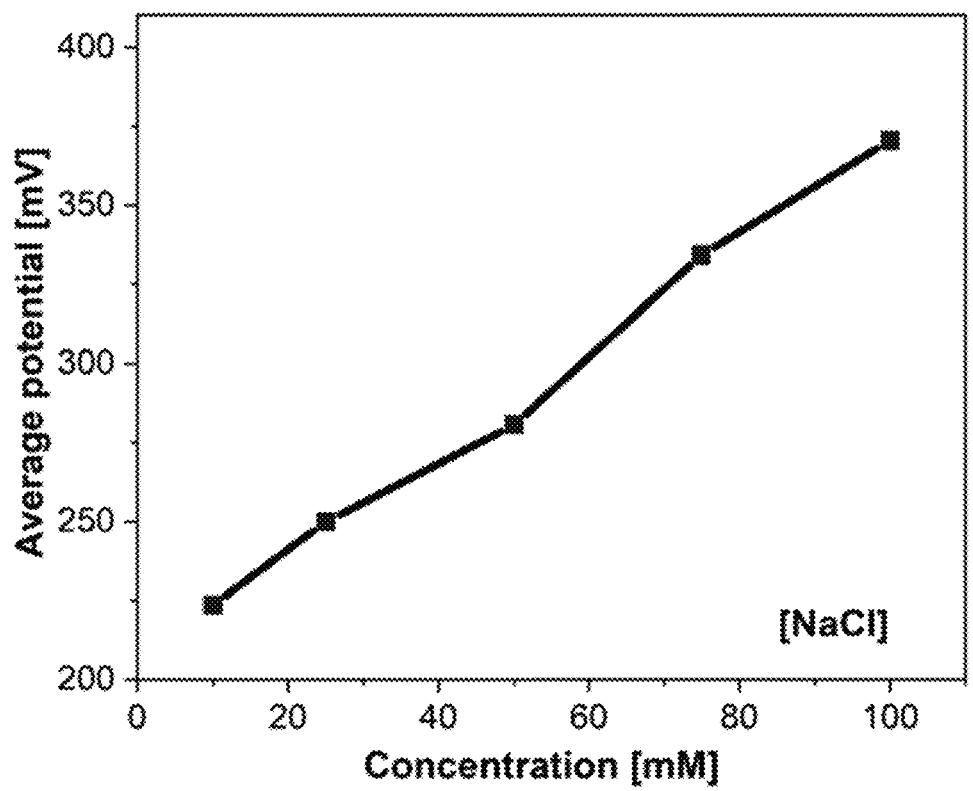
FIG. 6c shows the trend of the average amplitude of the signal generated as a function of the NaCl concentration of Example 2.
Figure 6D:
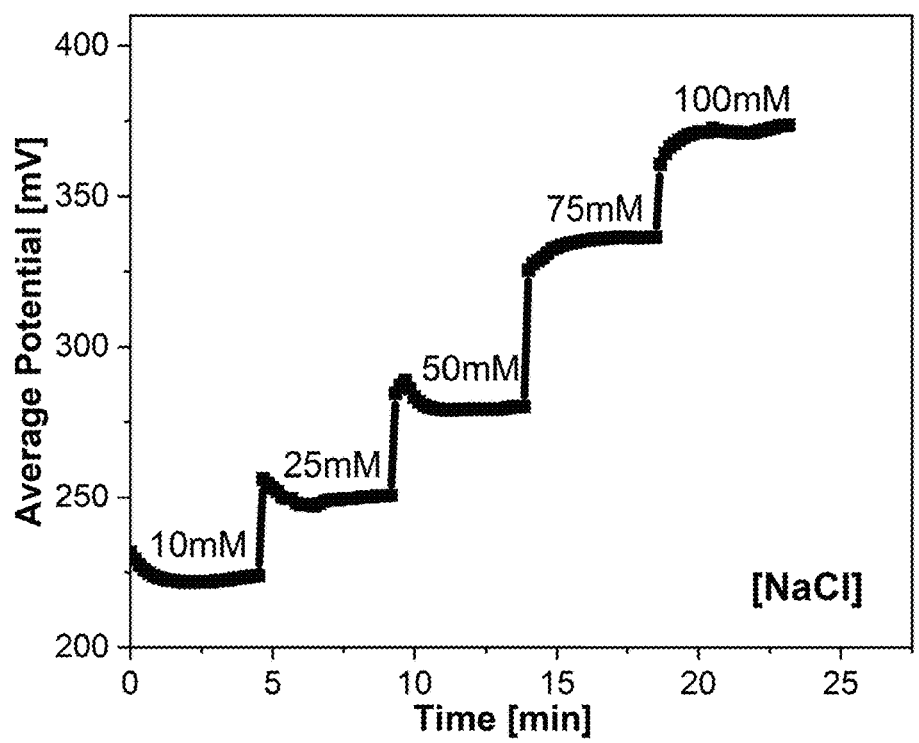
FIG. 6d shows the summary trend of the sensor response to the different NaCl concentrations of Example 2.

The two electrodes have an area of 1 $cm^2$ each, are incorporated in the polymer membrane produced and are electrically contacted by silver paint, conductive epoxy glue containing silver and silver conductive wires. The contacts were sealed by applying a thin layer of wax, as shown in FIG. 5.

Example 2—Sweat Sensor Made with PVDF, GNP and Nickel Microparticles

The sensor referred to in example 1, manufactured as described above, was subjected to several tests in order to study the different response to aqueous and artificial sweat solutions with different NaCl concentration, i.e., 10 mM, 25 mM, 50 mM, 75 mM, 100 mM. The concentration values were chosen so as to simulate the different NaCl concentrations in human sweat, both under normal and abnormal conditions (state of fatigue, dehydration, disease, etc.).

Immersion Test in Aqueous NaCl Solutions:

In order to characterize the response, example 1 was immersed in aqueous solutions with different NaCl concentrations for about 5 minutes and the voltage signal produced was measured with the aid of a voltmeter connected with a computer for data acquisition, as diagrammatically shown in FIG. 6 (*a*). The measurements were made three times and the average potential was determined at each concentration, in order to verify the reproducibility of the response.

FIG. 6(*b*) shows the amplitude of the voltage signal generated with respect to the immersion time, varying from zero (test start) to five minutes (test end). The graph indicates that the signal generated is almost constant and the amplitude thereof is proportional to the NaCl concentration in the saline solution. Furthermore, from FIG. 6(*c*), which shows the average value of the voltage signal generated as a function of concentration, it is clear that the dependence of the amplitude of the signal generated with respect to the NaCl concentration in the solution is linear. The whole is summarized in FIG. 6(*d*).

The performance of the sensor is summarized in Table 1, which shows for each NaCl concentration the average value of the voltage signal generated and the relative standard deviation, always less than 10% of the average value.

TABLE 1

| Concentration [mM] | Log C [mM] | Average potential [mV] | Standard deviation [mV] | Sensitivity [mV/log[C]] |
|---|---|---|---|---|
| 10 | 1 | 223.45 | 2.39 | — |
| 25 | 1.39 | 249.90 | 2.06 | 67.82 |
| 50 | 1.69 | 280.68 | 2.70 | 102.6 |
| 75 | 1.87 | 334.25 | 3.01 | 297.61 |
| 100 | 2 | 370.48 | 2.86 | 278.69 |

Artificial Sweat Immersion Test:

Artificial sweat was prepared at the laboratory of Nanotechnologies of Sapienza University of Rome following the European standard BS EN 1811: 2011. In summary, the artificial sweat solution was prepared by taking deionized water and mixing urea with it by magnetic stirring. Subsequently, sodium chloride, lactic acid, sodium hydroxide were added and thoroughly mixed with magnetic stirrer, paying attention to the pH of the final solution, which must be equal to 5.5±0.05.

The immersion test was performed in the artificial sweat obtained as mentioned above and adding 10 mM and 25 mM of NaCl thereto. To verify repeatability, the test was repeated three times (V1, V2, V3) and the average response value (Vg) was calculated.

Figure 7:
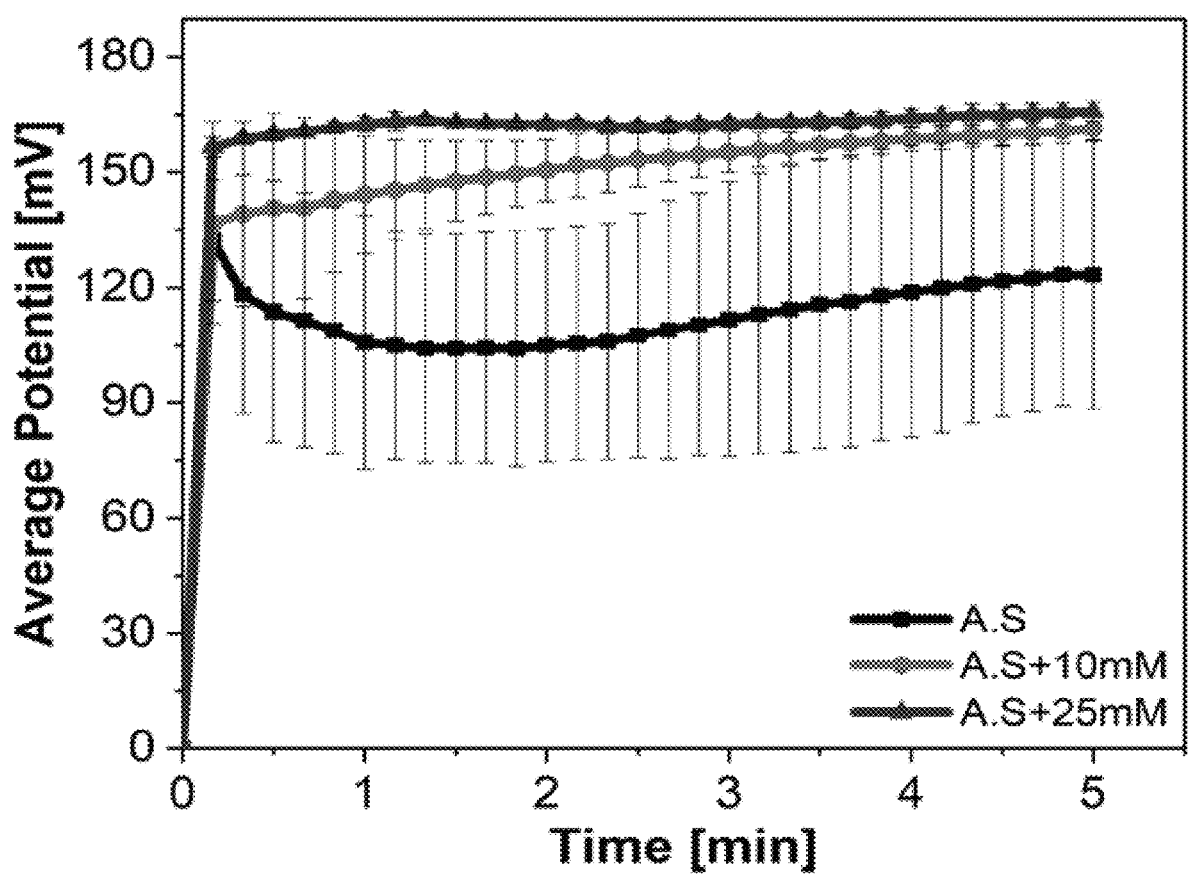
FIG. 7 shows the trend of the measured voltage signal as a function of time from the beginning to the end of the immersion test (five minutes) in the event of artificial sweat (A.S.), artificial sweat with the addition of 10 mM NaCl (A.S.+10 mM) and 25 mM NaCl (A.S.+25 mM) of Example 2.

FIG. 7 shows the voltage signal measured as a function of time from the beginning of the test (zero minutes) to the end of the test (five minutes) in the event of artificial sweat (A.S.), artificial sweat with the addition of 10 mM NaCl (A.S.+10 mM) and 25 mM NaCl (A.S.+25 mM).

Figure 8B:
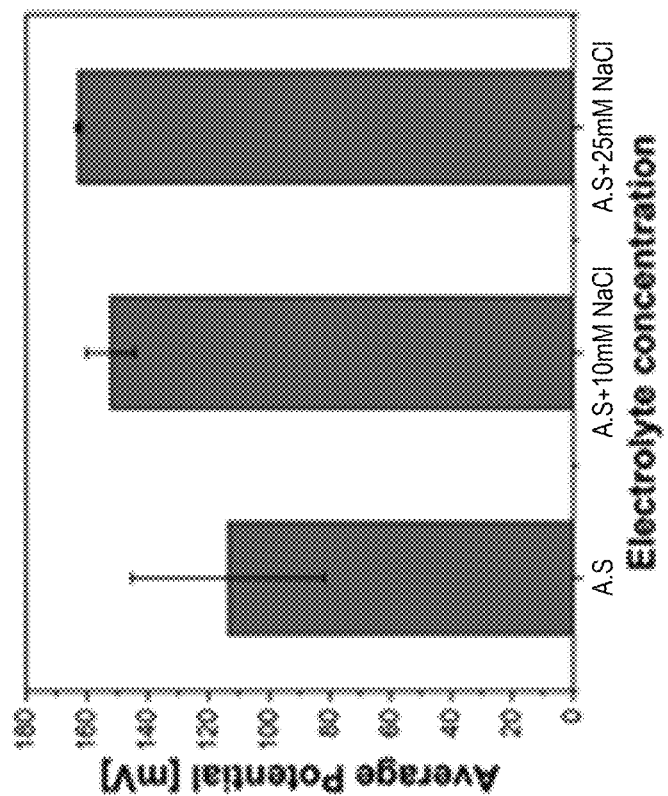
FIG. 8b shows the bar graph of the voltage signal averaged over time with respect to the NaCl concentration of Example 2.
Figure 8A:
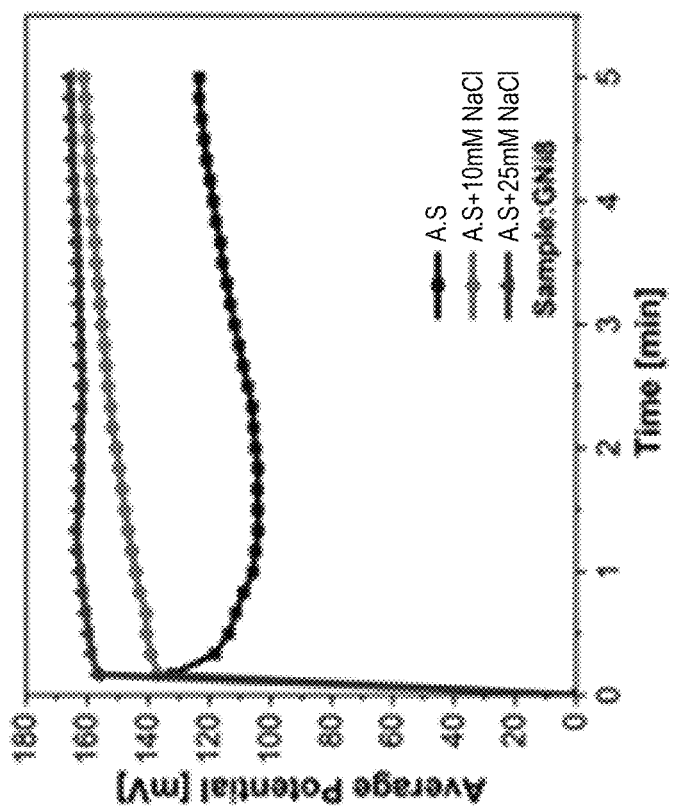
FIG. 8a shows the trend of the measured average voltage signal as a function of time of Example 2.

FIG. 8 (a) shows the average voltage signal measured as a function of time in the three cases while FIG. 8 (b) summarizes the signal averaged both with respect to the three measurements and with respect to time as a function of the NaCl concentration.

All this is summarized in Table 2, which shows the average values of the voltage signals generated for each NaCl concentration.

The results indicate that the measured voltage signal increases with increasing NaCl concentration in artificial sweat. Furthermore, the signal is repeatable, therefore the manufactured sensor is capable of detecting the salt concentration in artificial sweat.

TABLE 2

| Electrolyte Designation | Average Potential [mV] |
|---|---|
| Artificial sweat (A.S) | 113.57 ± 31.66 |
| A.S + 10 mM NaCl | 152.20 ± 8.03 |
| A.S + 25 mM NaCl | 162.75 ± 0.85 |

Figure 9:
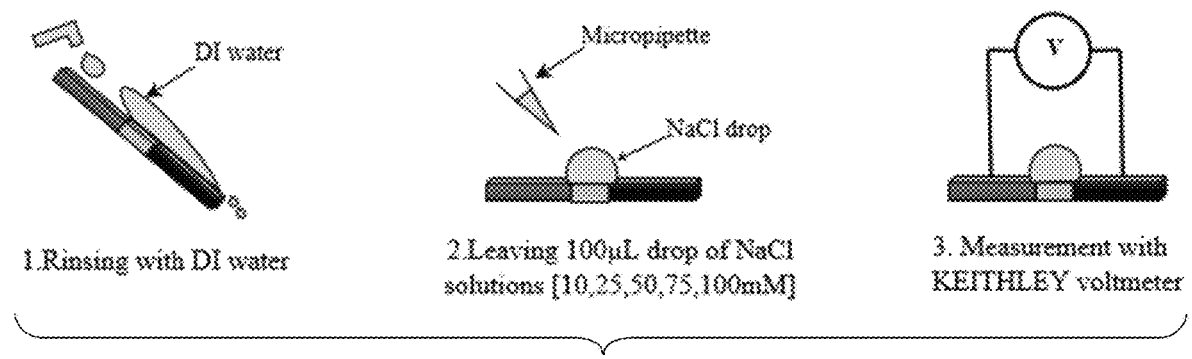
FIG. 9 shows a schematic diagram of the drop test of Example 2.

Drop Test with Aqueous NaCl Solutions:

This test was performed by releasing a 100 μl drop on the created example produced and measuring the voltage signal generated for about 5 minutes, as diagrammatically shown in FIG. 9. After the measurement, the drop was removed and the example was washed with deionized water.

The test was performed with deionized water (indicated with DI) and with solutions characterized by different NaCl concentrations, namely: 10 mM, 25 mM, 50 mM, 75 mM, 100 mM. In any case, the test was repeated three times, verifying the repeatability of the measurement.

Figure 10:
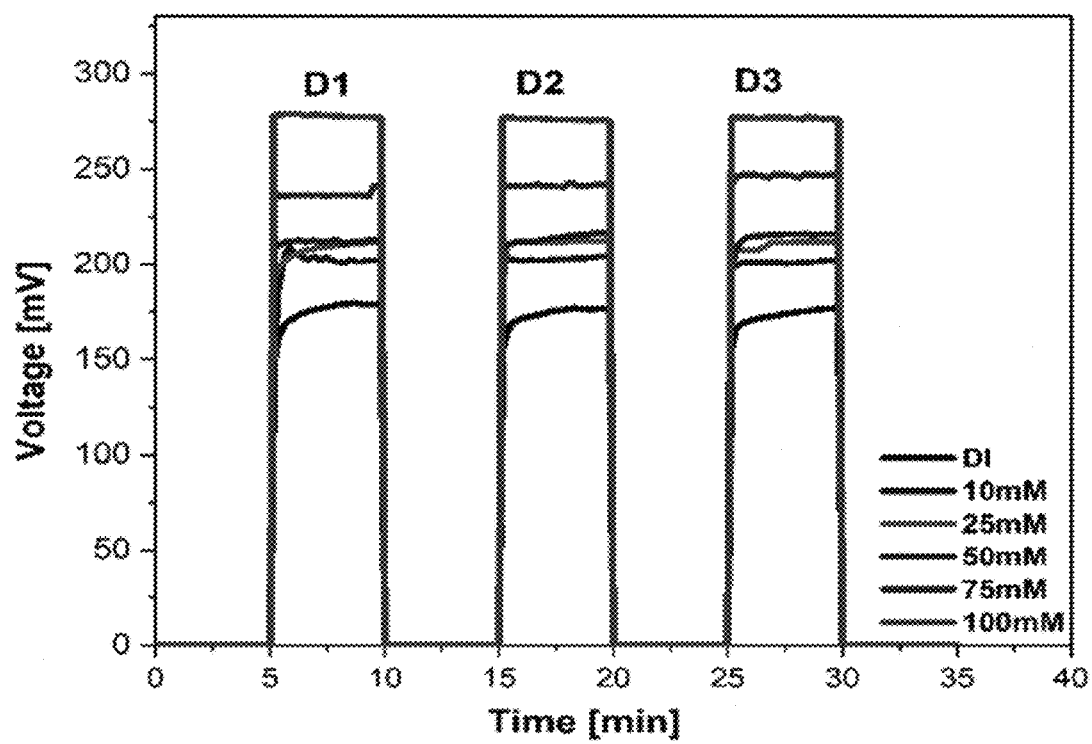
FIG. 10 shows the trend of the amplitude of the voltage signal generated by the three drops (D1, D2 and D3) as a function of time and for all the solutions analyzed in Example 2.

The test results are briefly shown in FIG. 10; in particular, the amplitude of the voltage signal generated by the three drops (D1, D2 and D3) is reported as a function of time and for all the solutions analyzed.

It can be seen that the measurements are repeatable and the different NaCl concentrations in the solution are clearly distinguishable from the signal amplitude.

Moreover, the signals corresponding to NaCl concentrations between 10 mM and 25 mM (i.e., the concentrations of chloride ions in the sweat of healthy individuals and under normal conditions) are clearly distinguishable from those generated in the presence of solutions with NaCl concentrations greater than 70 mM, typical for example in the sweat of individuals with dehydration phenomena or suffering from diseases such as cystic fibrosis, as discussed above.

TABLE 3

| Concentration [mM] | Average Potential [mV] | Standard deviation [mV] |
|---|---|---|
| DI | 173.69 | 0.69 |
| 10 | 201.97 | 1.84 |
| 25 | 209.55 | 1.32 |
| 50 | 213.38 | 1.45 |
| 75 | 241.60 | 0.46 |
| 100 | 276.97 | 0.11 |

The average numerical values and the relative standard deviations of the voltage signals generated for the different NaCl concentrations are shown in Table 3.

Figure 11:
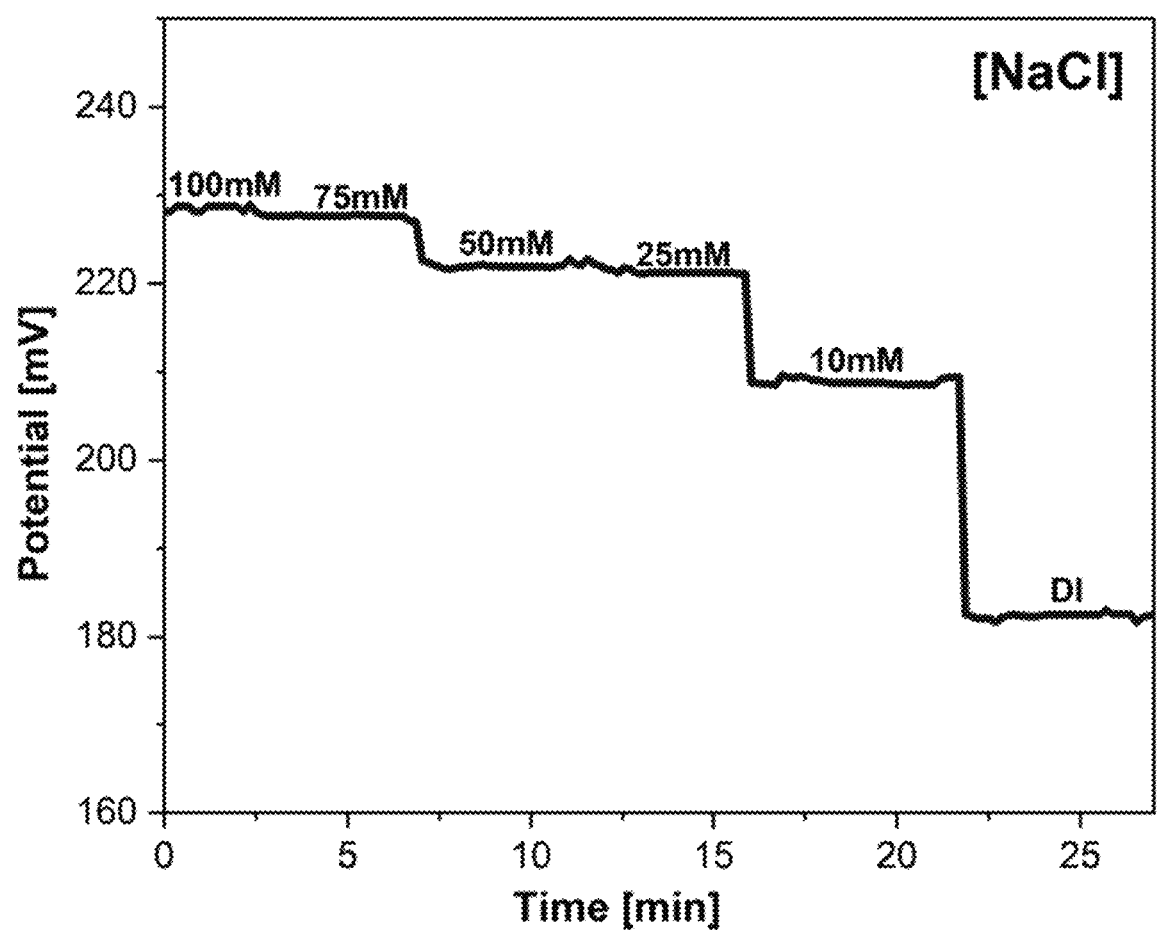
FIG. 11 shows the trend of the voltage signal amplitude as a function of time in Example 2.

Subsequently, in order to reproduce real operating conditions, the test was repeated without washing the embodiment example between one drop and the other. That is, the drop of the NaCl solution under consideration was deposited and then removed simply by tilting the example itself, without either drying or washing the invention between one drop and the other. The results are shown in FIG. 11, where the amplitude of the voltage signal generated is reported as a function of time. It should be noted that the stress response of the produced example is proportional to the NaCl concentration in the droplets of aqueous solutions.

The average numerical values and the relative standard deviations of the voltage signals generated for the different NaCl concentrations are shown in Table 4.

TABLE 4

| Concentration [mM] | Potential [mV] | Standard deviation [mV] |
|---|---|---|
| DI | 182.31 | 0.27 |
| 10 | 208.89 | 0.37 |
| 25 | 221.51 | 0.48 |
| 50 | 222.02 | 0.29 |
| 75 | 227.58 | 0.18 |
| 100 | 228.49 | 0.32 |

Figure 12A:
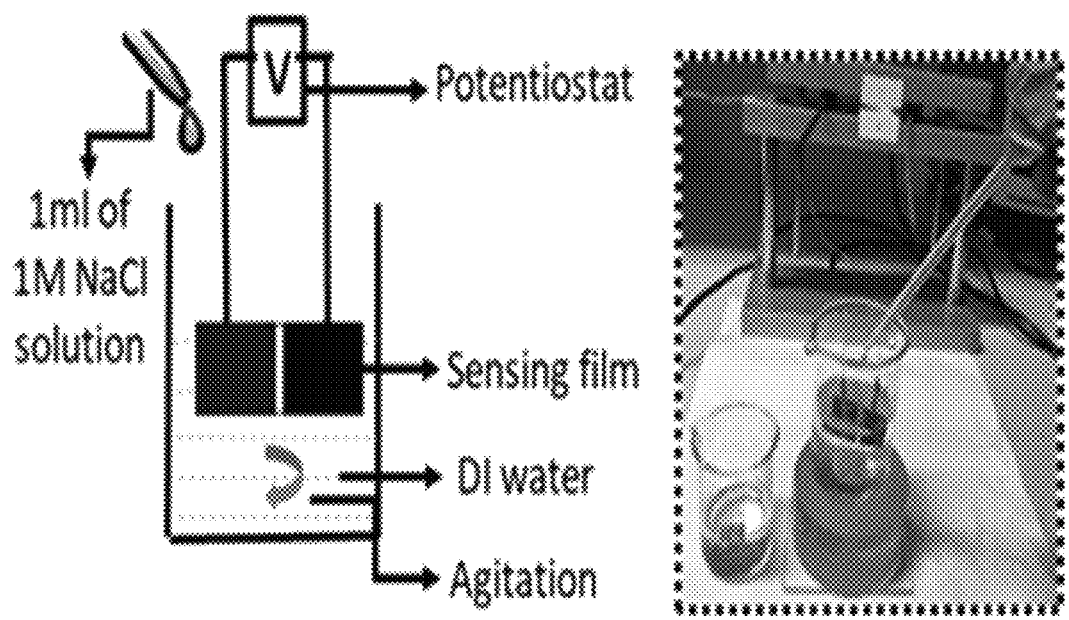
FIG. 12a shows the conceptual diagram of the aqueous solution immersion test with increasing NaCl concentration relative to Example 2.

Immersion Test in Aqueous Solution with Increasing NaCl Concentration:

This test was performed by immersing the sensor in 50 ml of deionized water, to which 1 ml drops of 1M NaCl solution were added every two minutes, as shown in FIG. 12(a). It was calculated that each drop of 1 ml of 1M NaCl solution increases the concentration of the solution by 20 mM NaCl.

Figure 12B:
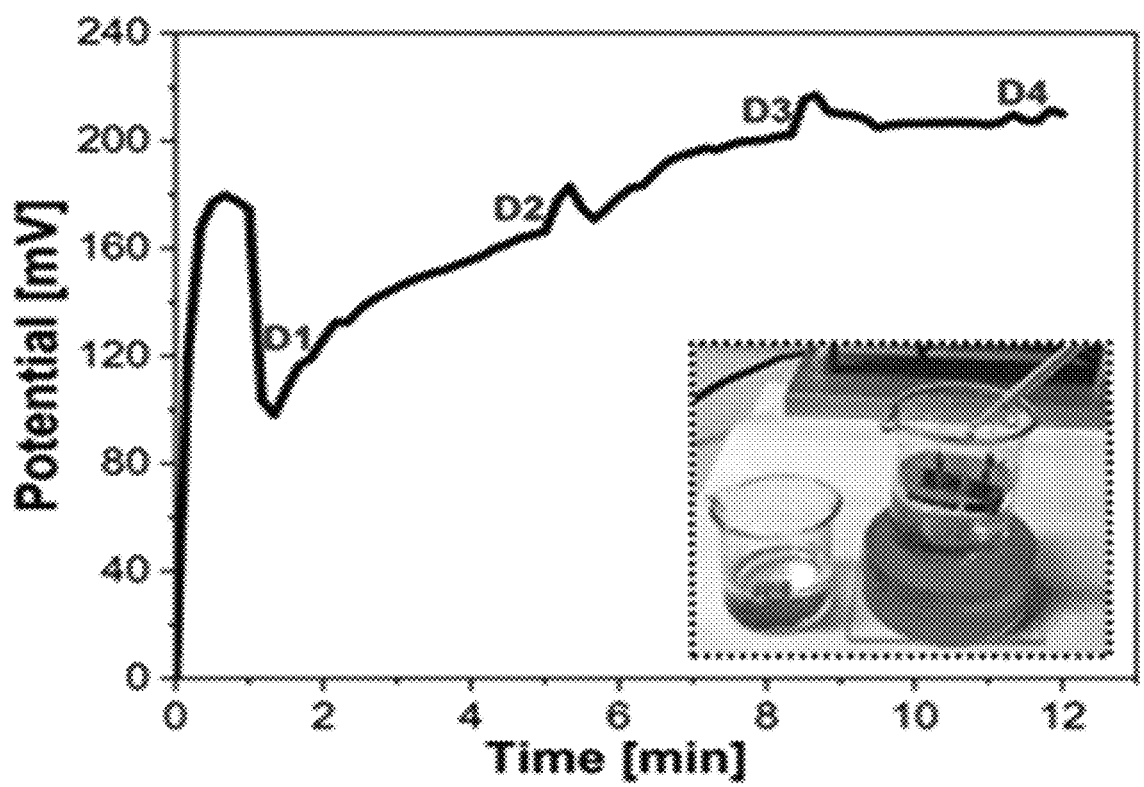
FIG. 12b shows the trend of the live signal with respect to the time of the aqueous immersion test with increasing NaCl concentration relative to Example 2.

FIG. 12(b) shows the measured voltage signal with respect to time. The 1 ml drops of 1M NaCl solution are numbered with D1, D2, D3 and D4.

The increase in NaCl concentration in the solution following the addition of the 1 ml drops of 1M NaCl solution is shown in Table 5.

TABLE 5

| Number of drops | Amount of solution (ml) | Amount of salt (g) | Concentration [mM] |
|---|---|---|---|
| D0 | 50 | 0 | 0 |
| D1 | 51 | 0.05844 | 19.6 |
| D2 | 52 | 0.11688 | 39.2 |
| D3 | 53 | 0.17532 | 58.8 |
| D4 | 54 | 0.23376 | 78.4 |

From the aforesaid FIG. 12(b) it can be seen that the measured potential gradually increases when the salt concentration increases in the deionized water in which the sensor is immersed. Therefore, the object of the present invention can be useful for the real-time analysis of the NaCl concentration in sweat during, for example, exercise.

Wettability Test:

In order to verify the hydrophilicity of the invention, 2.5 μl droplets of the NaCl solutions considered so far, i.e., with concentrations ranging from 10 mM to 100 mM, were deposited on the above example, as described above.

Once the drop was deposited, several photographic images were taken with an appropriate measurement set-up and the contact angle was measured therefrom by post-processing the collected images. By way of comparison, the test was also performed for deionized water (DI).

Figure 13A:
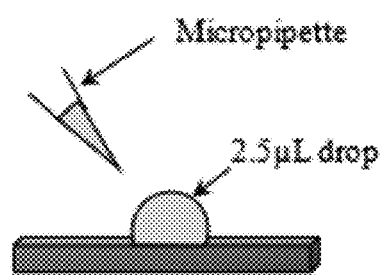
FIG. 13a shows the diagrammatic image of the wettability test relative to Example 2.
Figure 13B:
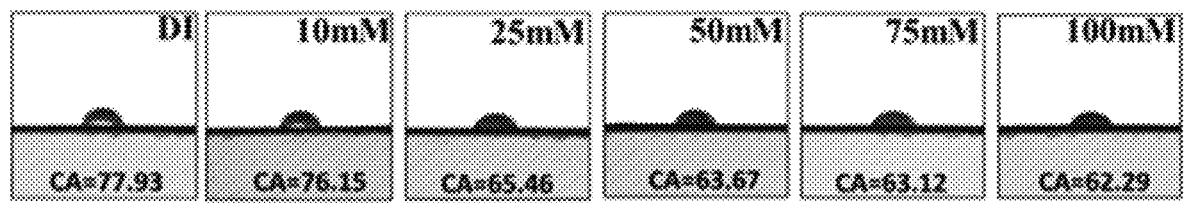
FIG. 13b shows the images collected for each NaCl solution considered (from 10 mM to 100 mM) and for deionized water (DI), with an indication at the bottom of each image of the average value of the contact angle (CA) measured relative to Example 2.

FIG. 13 (a) shows a diagram of the test performed while FIG. 13 (b) summarizes the images collected for each solution considered and reports the average value of the contact angle (CA) measured.

Table 6 below shows all the average values of the contact angles with the relative standard variations. It should be noted that the contact angle decreases slightly as the NaCl concentration increases. However, this increase does not affect the hydrophilicity of the invention. It can therefore be concluded that the product according to the present invention is hydrophilic, regardless of the concentration of the considered saline solutions.

TABLE 6

| Concentration of NaCl [mM] | Average Contact angle θ [°] |
|---|---|
| DI | 79.15 ± 1.53° |
| 10 | 78.97 ± 1.91° |
| 25 | 66.69 ± 1.08° |
| 50 | 64.27 ± 0.54° |
| 75 | 63.64 ± 0.45° |
| 100 | 62.06 ± 0.25° |

Figure 14:
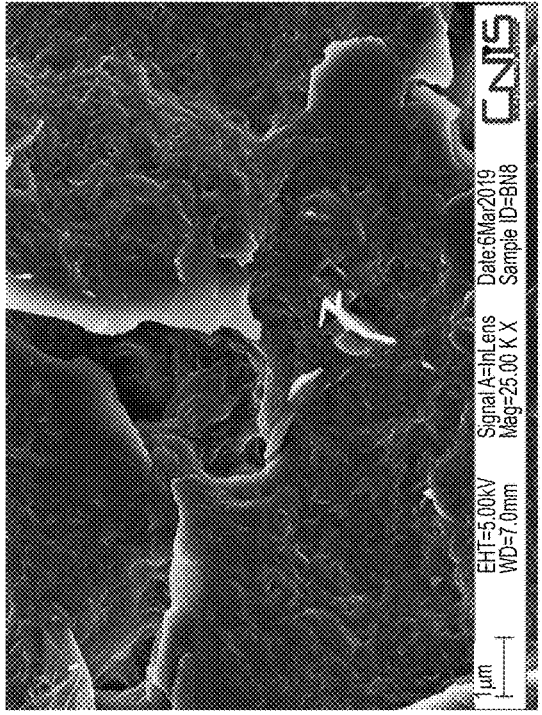
FIG. 14 shows the SEM images at different magnifications of the invention before it is put in contact with aqueous NaCl solutions and relative to Example 2.
Figure 14:
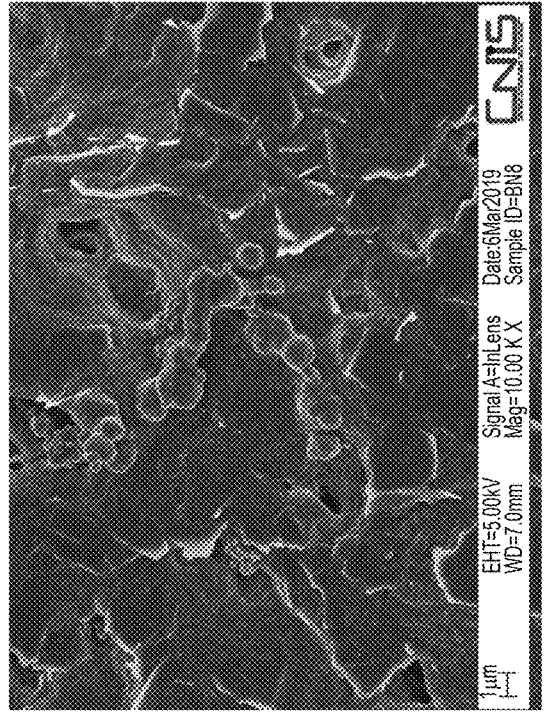
Figure 14:
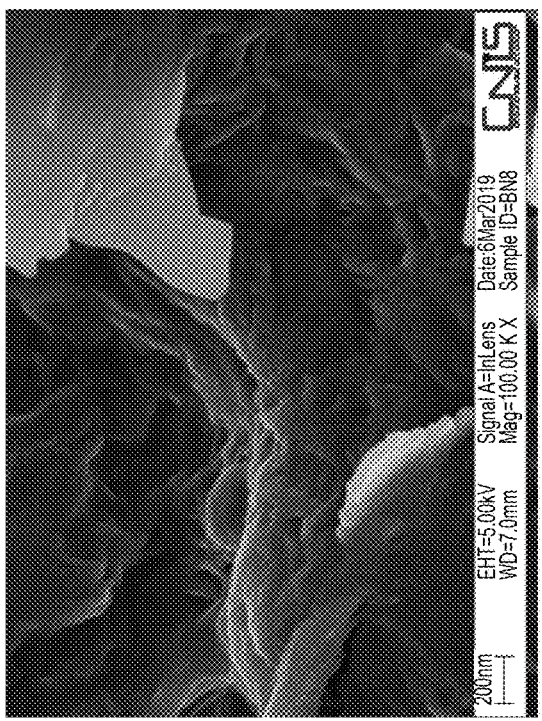
Figure 14:
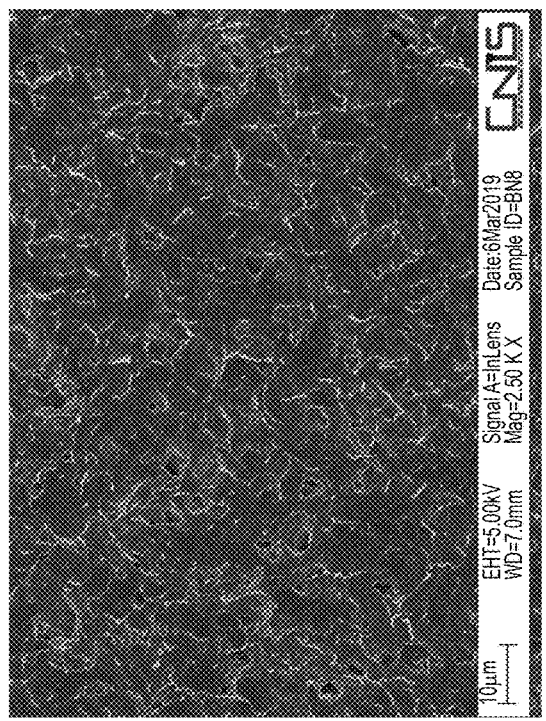
Figure 14:
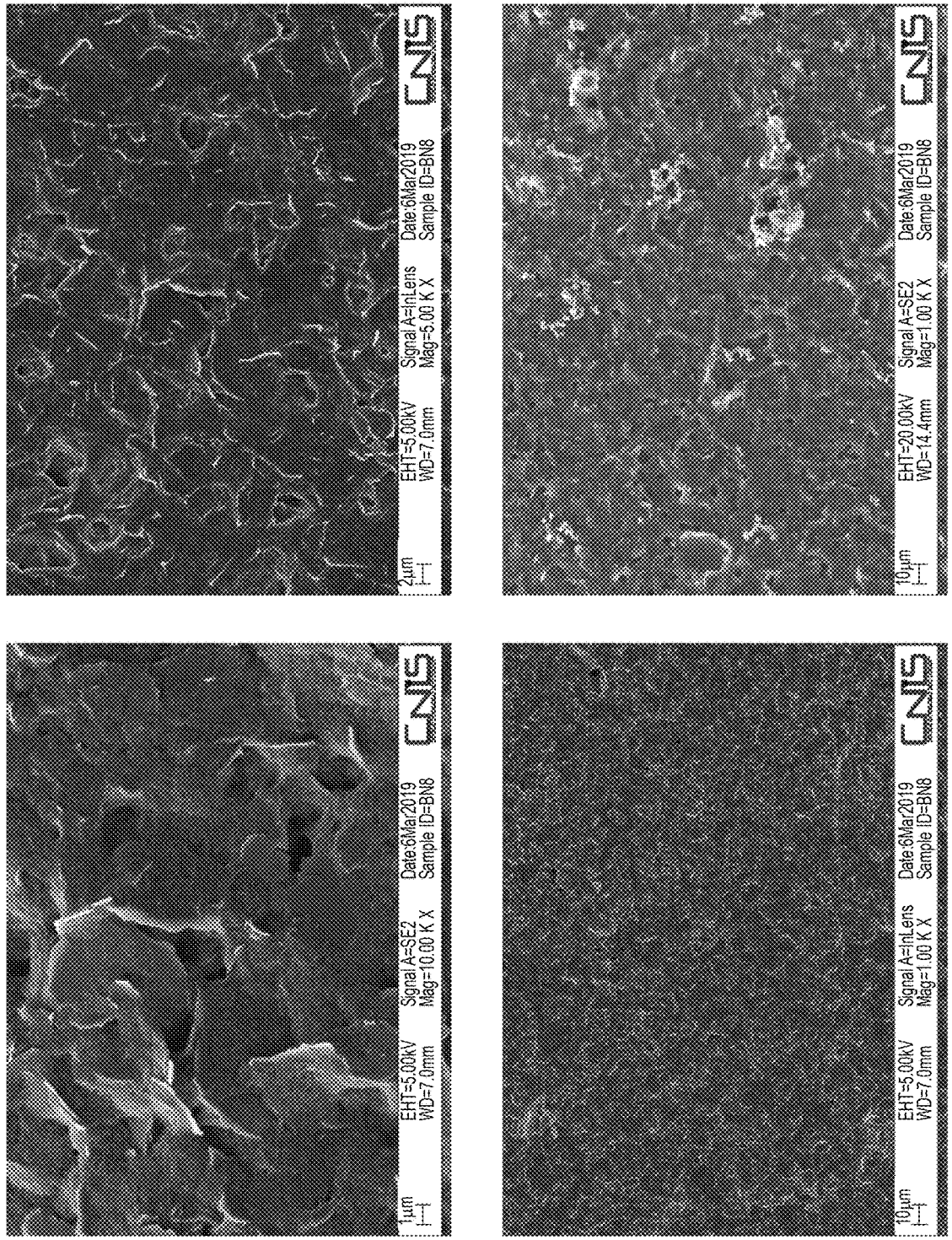
Figure 15:
FIG. 15 shows the SEM images at different magnifications of the invention after testing with aqueous NaCl solutions and relative to Example 2.
Figure 15:
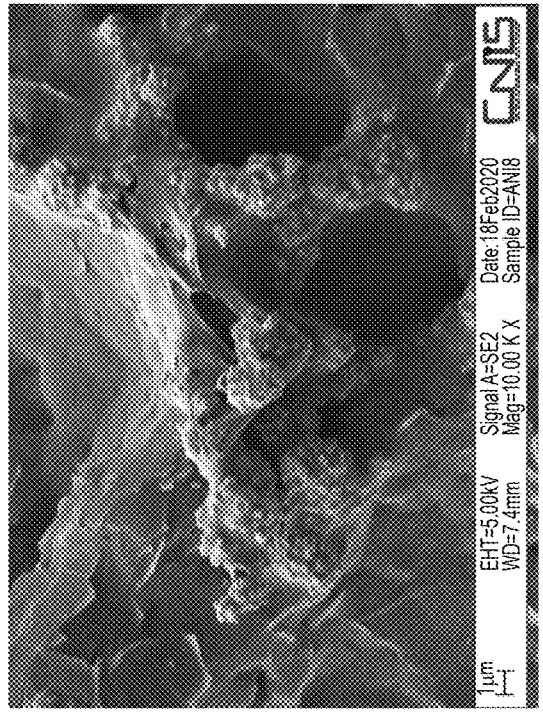
Figure 15:
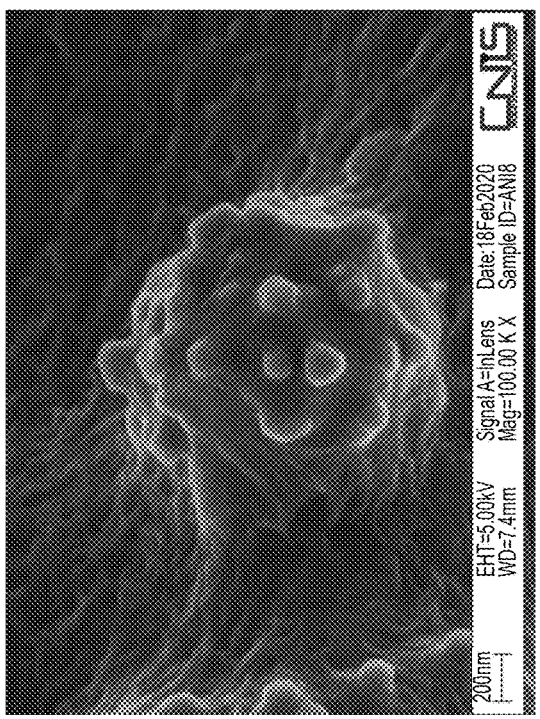
Figure 15:
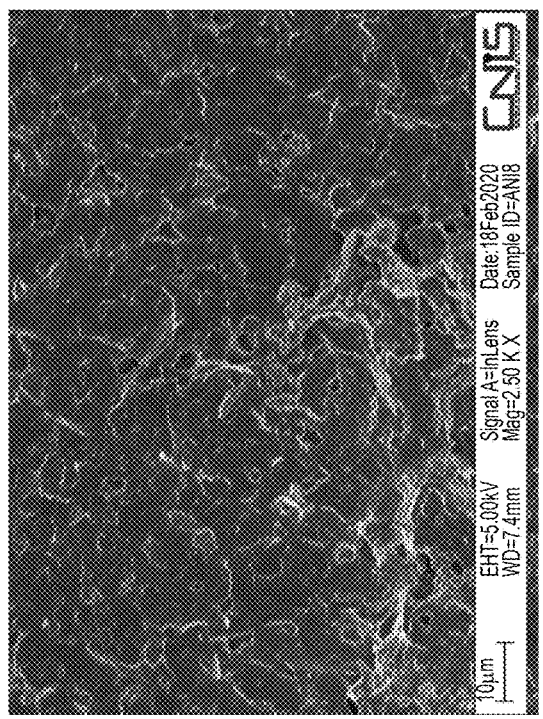
Figure 15:
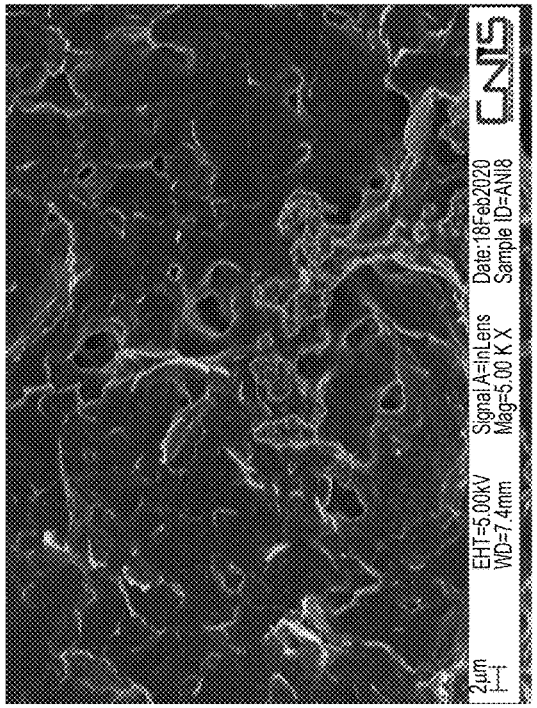
Figure 15:
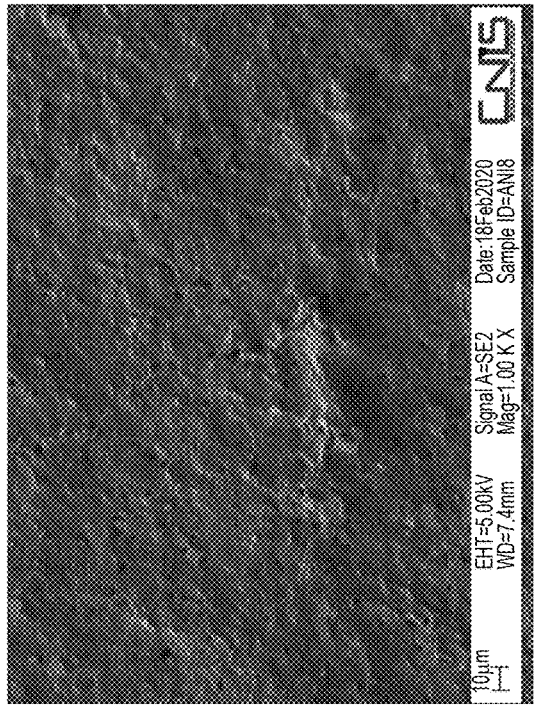
Figure 15:
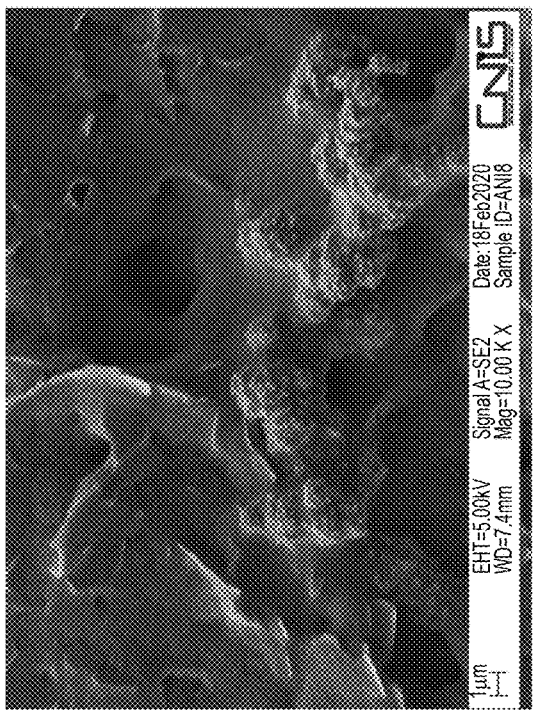
Figure 15:
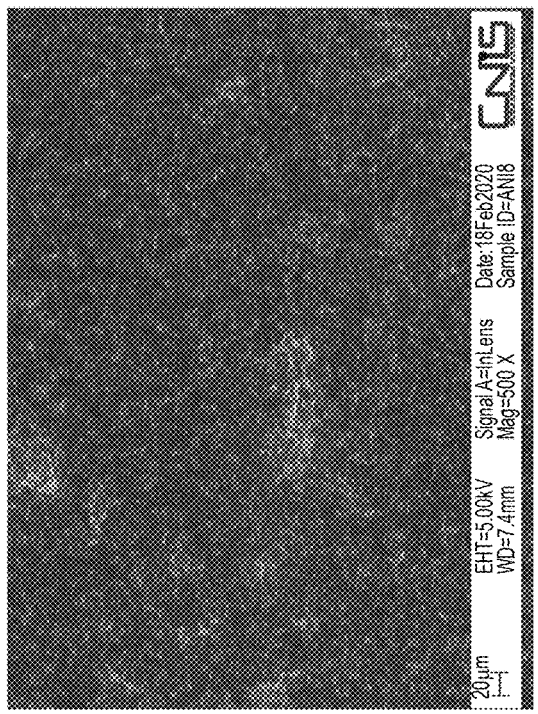

Morphological Characterization:

In order to verify any changes in the material following exposure to aqueous NaCl solutions, the sample was analyzed with an electron scanning microscope (SEM) at the Nanotechnologies Laboratory of Sapienza University of Rome. In particular, the sample was analyzed before and after the various tests. FIG. 14 shows the SEM images at different magnifications taken before the sample came into contact with the different aqueous NaCl solutions used for the characterization. Conversely, FIG. 15 shows the SEM images of the same produced sample after the various characterizations described. It should be noted that the GNPs and metal nickel microparticles have good adhesion in the polymer matrix. It is also apparent that the morphology of the film does not change after the electrochemical test in saline solution.

Example 3—Sweat Sensor Made with PVDF, GNP and Aluminum by Spin-Coating

By way of explanation, another sweat sensor such as that shown in FIG. 2 (a) was made. In this example, one of the electrodes thereof was manufactured using the spin-coating technique on a portion of a commercial aluminum sheet.

Figure 16:
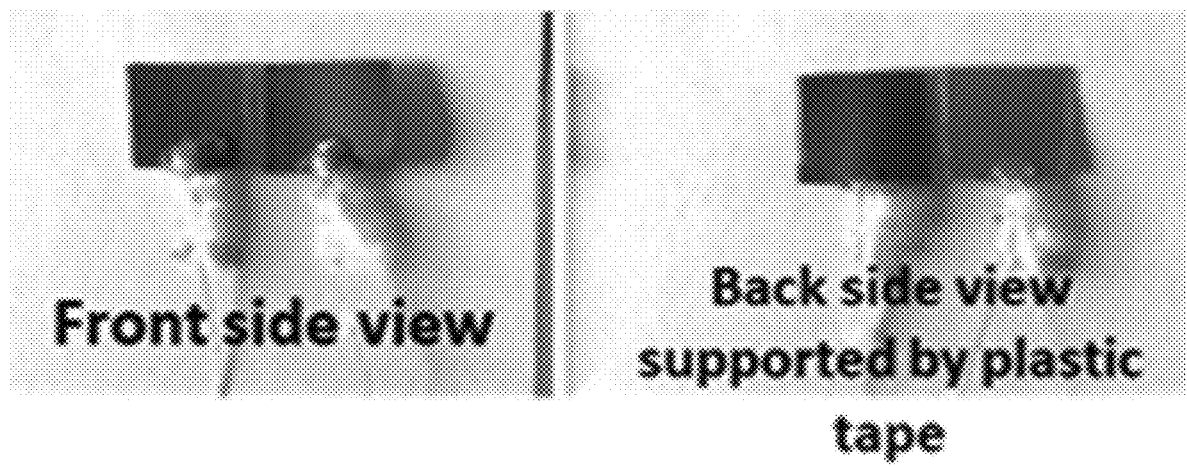
FIG. 16 shows the invention made according to Example 3.

The two electrodes have an area of 1 cm$^2$ each, are incorporated in the polymer sheet produced and are electrically contacted by silver paint, conductive epoxy glue containing silver and silver conductive wires. The contacts were sealed by applying a thin layer of wax, as shown in FIG. 16.

Example 4—Sweat Sensor Made with PVDF, GNP and Aluminum by Spin-Coating

The sensor referred to in example 3, manufactured as described above, was subjected to several tests in order to study the different response to aqueous and artificial sweat solutions with different NaCl concentration, i.e., 10 mM, 25 mM, 50 mM, 75 mM, 100 mM. The concentration values were chosen so as to simulate the different NaCl concentrations in human sweat, both under normal and abnormal conditions (state of fatigue, dehydration, disease, etc.).

Immersion Test in Aqueous NaCl Solutions:

In order to characterize the response, the sensor of example 3 was immersed in aqueous solutions with different NaCl concentrations for about 5 minutes and the voltage signal produced was measured with the aid of a voltmeter connected with a computer for data acquisition, as diagrammatically shown in FIG. 6 (a). The measurements were made three times and the average potential was determined at each concentration, in order to verify the reproducibility of the response.

Figure 17:
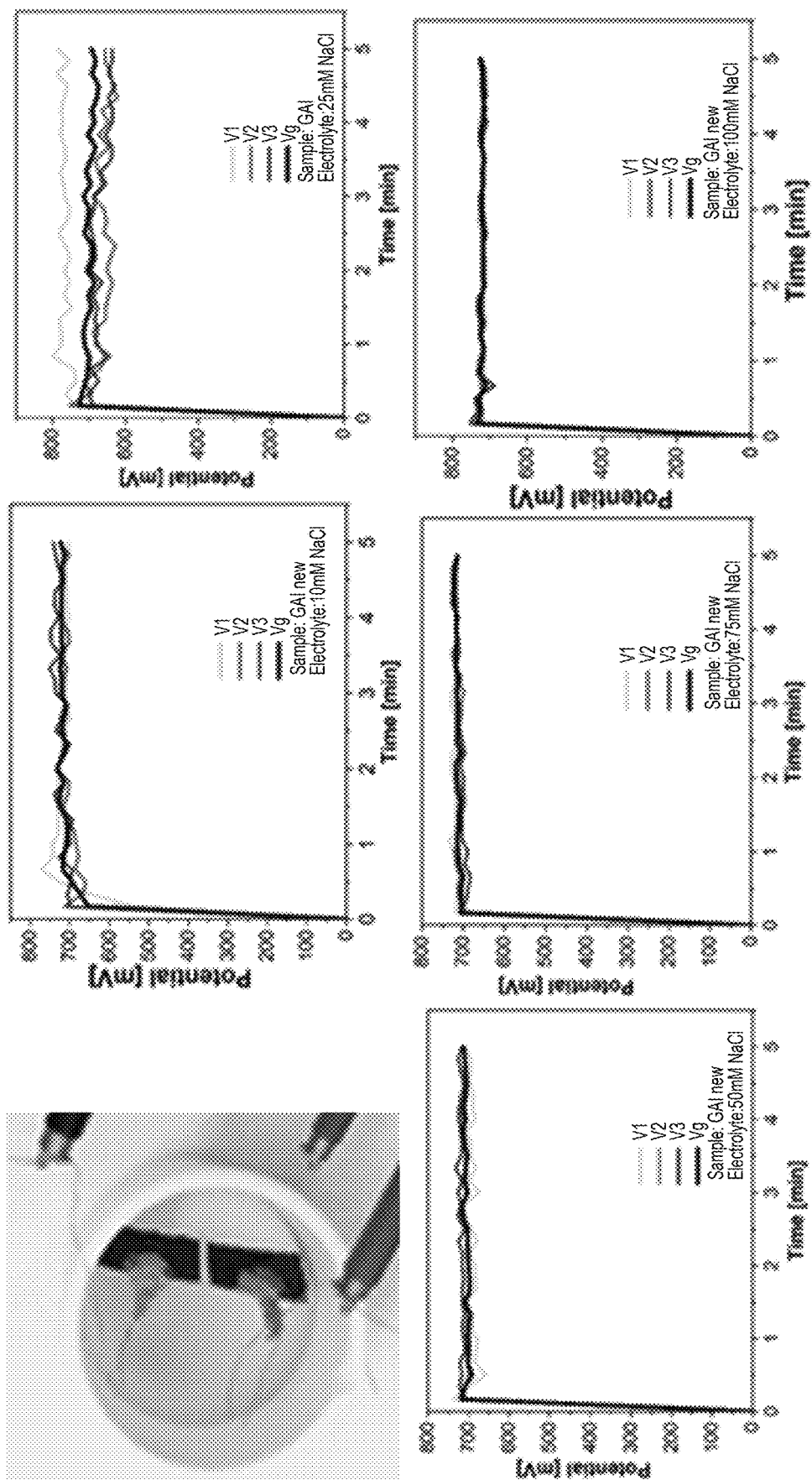
FIG. 17 shows the trends of the amplitude of the voltage signal generated with respect to the immersion time varying from zero (test start) to five minutes (test end) for the different solutions considered and relative to Example 4.

FIG. 17 shows the amplitude of the voltage signal generated with respect to the immersion time, varying from zero (test start) to five minutes (test end). The graph indicates that the signal generated is almost constant and the amplitude thereof is proportional to the NaCl concentration in the saline solution.

The average numerical values of the voltage signals generated for each NaCl concentration are shown in Table 7, together with the standard deviations. It should be noted that the average value of the voltage signal generated as a function of concentration increases with increasing NaCl concentration.

TABLE 7

| Concentration [mM] | Average Potential [mV] |
|---|---|
| 10 | 713.35 ± 8.07 |
| 25 | 698.72 ± 58.35 |
| 50 | 705.86 ± 11.73 |
| 75 | 713.34 ± 6.61 |
| 100 | 720.89 ± 0.89 |

Drop Test with Aqueous NaCl Solutions:

This test was performed by releasing a 100 μl drop on the example produced and measuring the voltage signal generated for about 5 minutes, as diagrammatically shown in FIG. 9. After the measurement, the drop was removed and the example was washed with deionized water.

The test was performed with deionized water (indicated with DI) and with solutions characterized by different NaCl concentrations, namely: 10 mM, 25 mM, 50 mM, 75 mM, 100 mM. In any case, the test was repeated three times, verifying the repeatability of the measurement.

Figure 18:
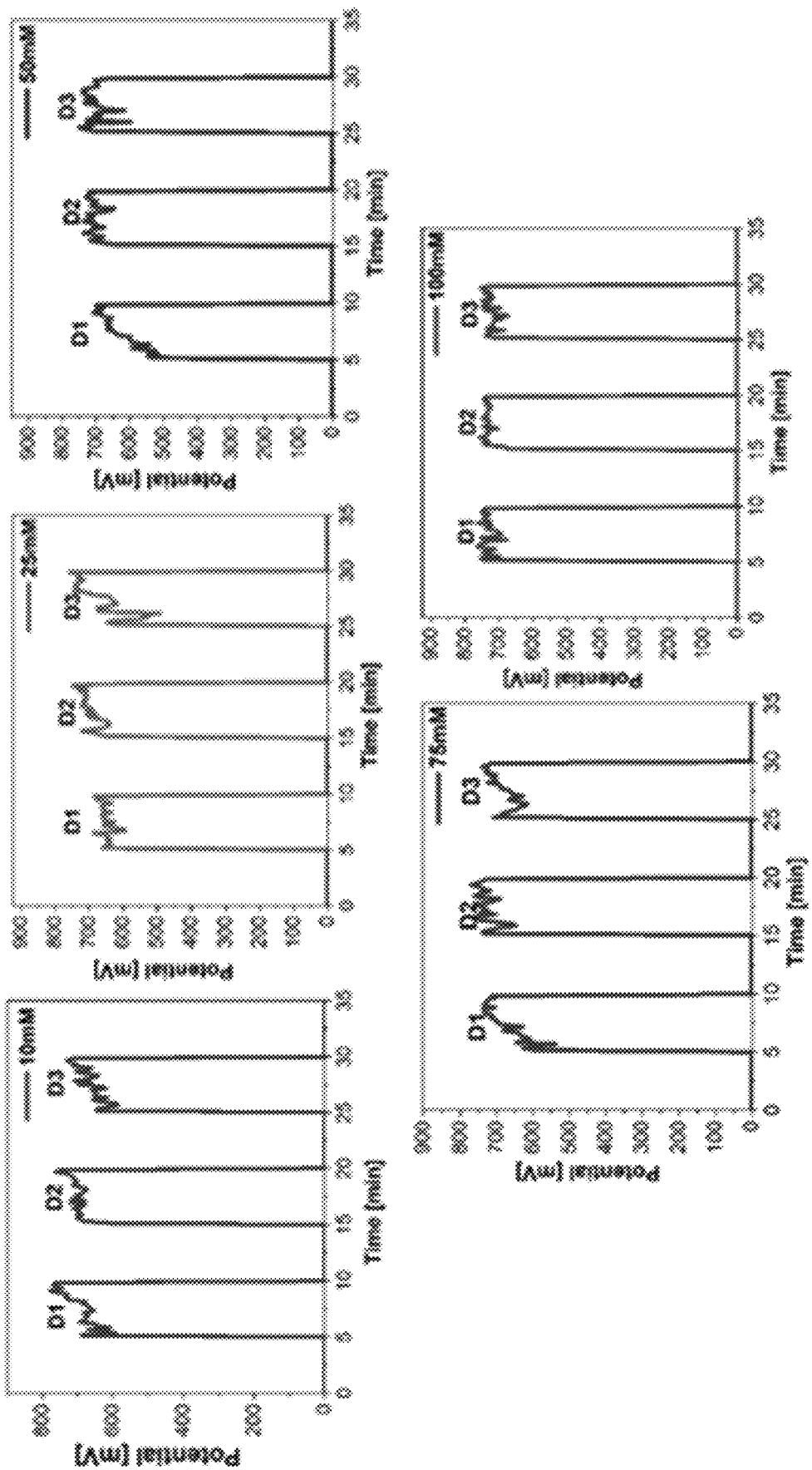
FIG. 18 shows the trends of the voltage signal generated with respect to the immersion time for the different solutions considered relative to the drop test with aqueous NaCl solutions of Example 4.

The results obtained are reported in FIG. 18. It should be noted that the signal generated increases with increasing NaCl concentration, as can be seen by comparing the numerical values shown in Table 8, where the average values of the voltage signals generated for each NaCl concentration are reported.

TABLE 8

| Concentration [mM] | Average Potential [mV] |
|---|---|
| 10 | 690.55 ± 14.43 |
| 25 | 701.69 ± 36.90 |
| 50 | 679.06 ± 31.54 |
| 75 | 696.26 ± 28.01 |
| 100 | 732.41 ± 8.33 |

Immersion Test in Aqueous Solution with Increasing NaCl Concentration:

This test was performed by immersing the sensor in 50 ml of deionized water, to which 1 ml drops of 1M NaCl solution were added every two minutes, as shown in FIG. 12(a). It was calculated that each drop of 1 ml of 1M NaCl solution increases the concentration of the solution by 20 mM NaCl.

Figure 19:
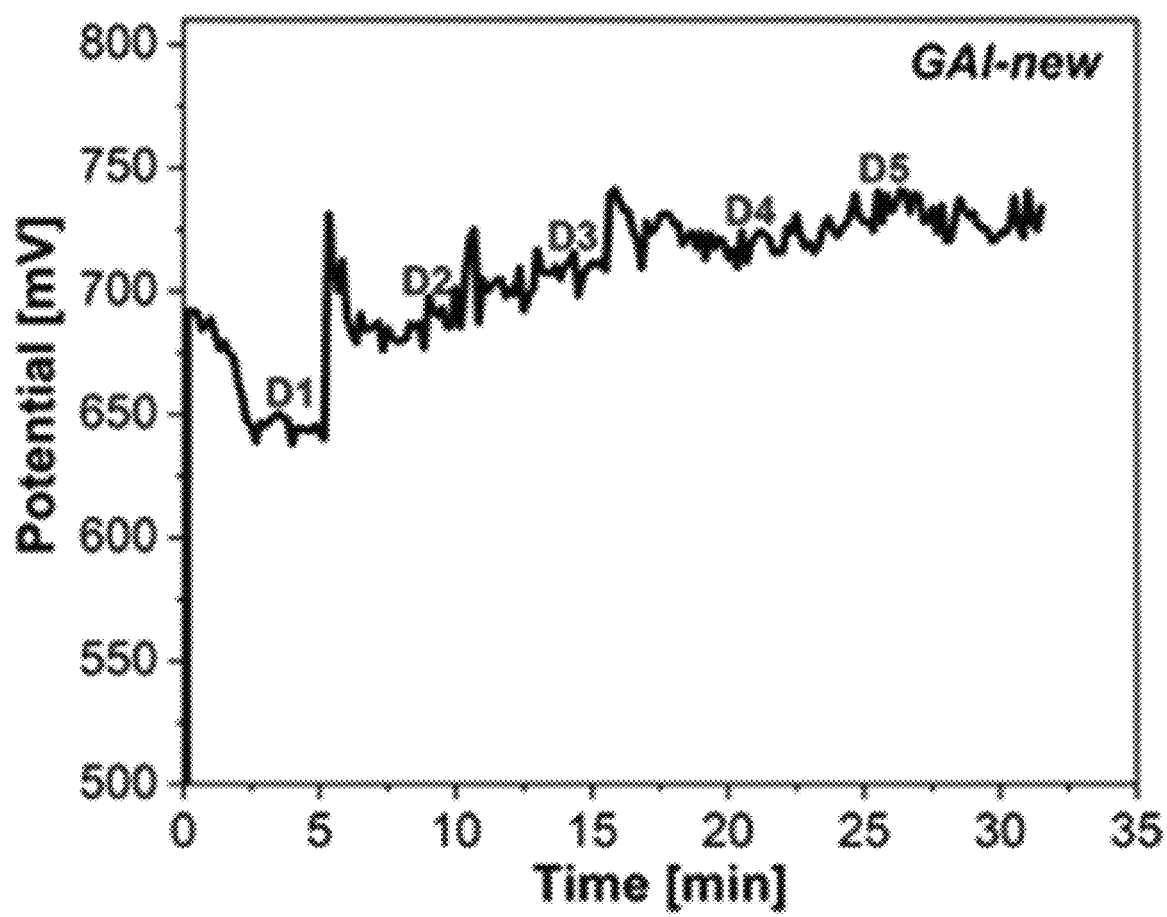
FIG. 19 shows the trend of the measured voltage signal with respect to the time of the immersion test in aqueous solution with increasing NaCl concentration of Example 4.

FIG. 19 shows the measured voltage signal with respect to time. The 1 ml drops of 1M NaCl solution are numbered with D1, D2, D3, D4 and D5.

The increase in NaCl concentration in the solution following the addition of the 1 ml drops of 1M NaCl solution is shown in Table 9.

TABLE 9

| Number of drops | Amount of solution (ml) | Amount of salt (g) | Concentration [mM] |
|---|---|---|---|
| D0 | 50 | 0 | 0 |
| D1 | 51 | 0.05844 | 19.6 |
| D2 | 52 | 0.11688 | 39.2 |
| D3 | 53 | 0.17532 | 58.8 |
| D4 | 54 | 0.23376 | 78.4 |
| D5 | 55 | 0.29223 | 98 |

It can be seen that the measured potential gradually increases when the salt concentration increases in the deionized water.

Figure 20:
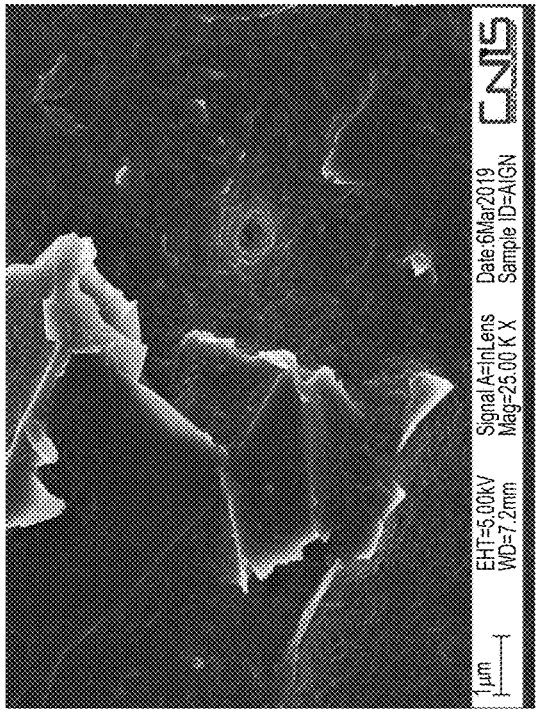
FIG. 20 shows the SEM images at different magnifications of the invention before it is put in contact with aqueous NaCl solutions and relative to Example 4.
Figure 20:
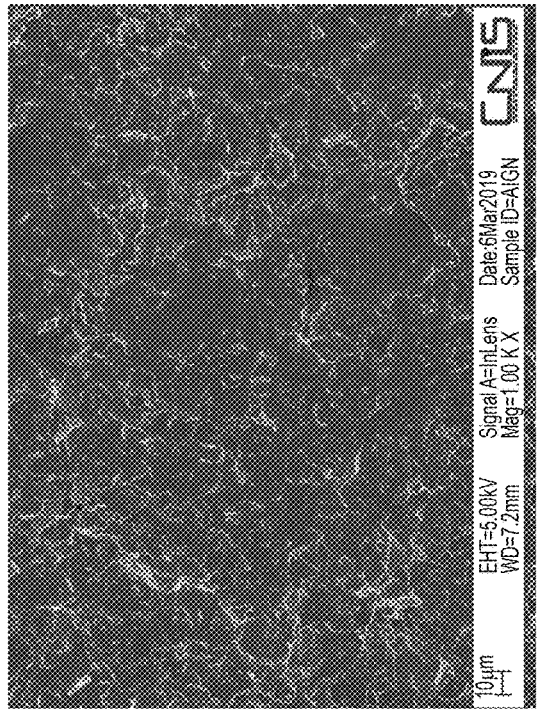
Figure 20:
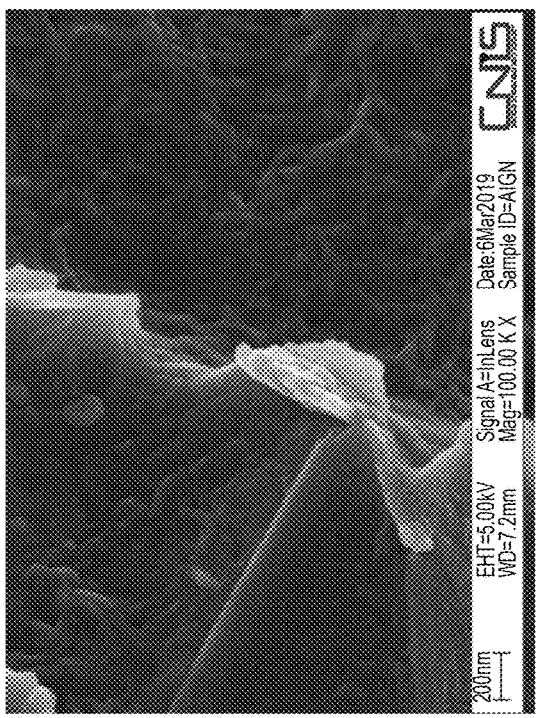
Figure 20:
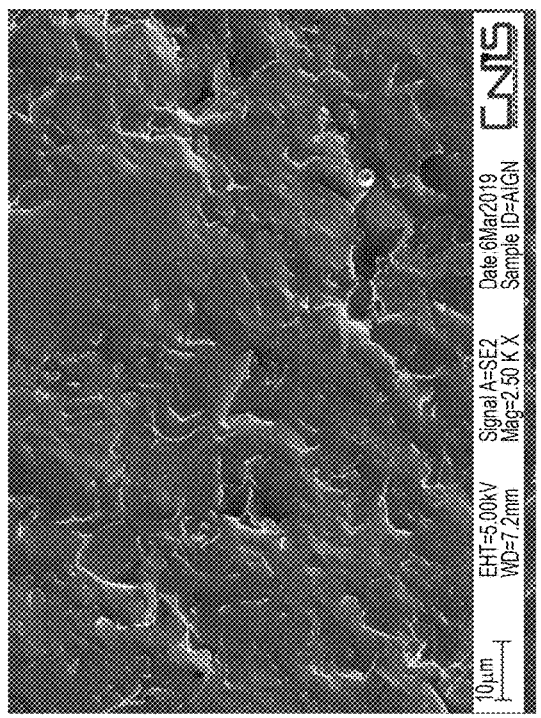
Figure 20:
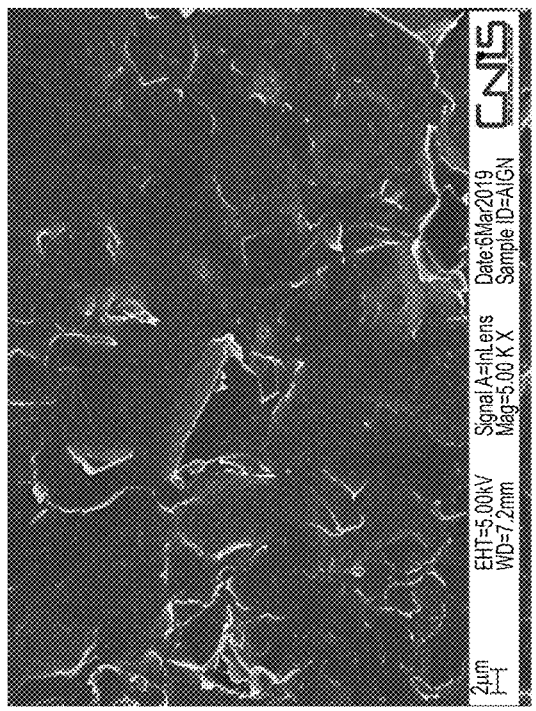
Figure 20:
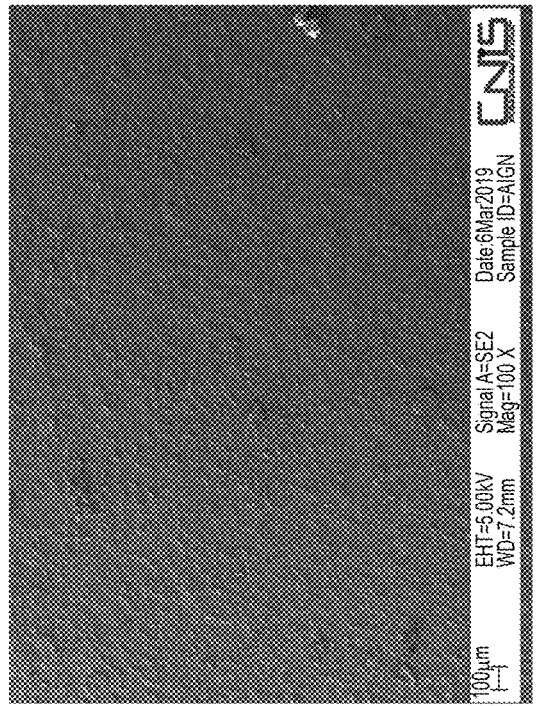
Figure 20:
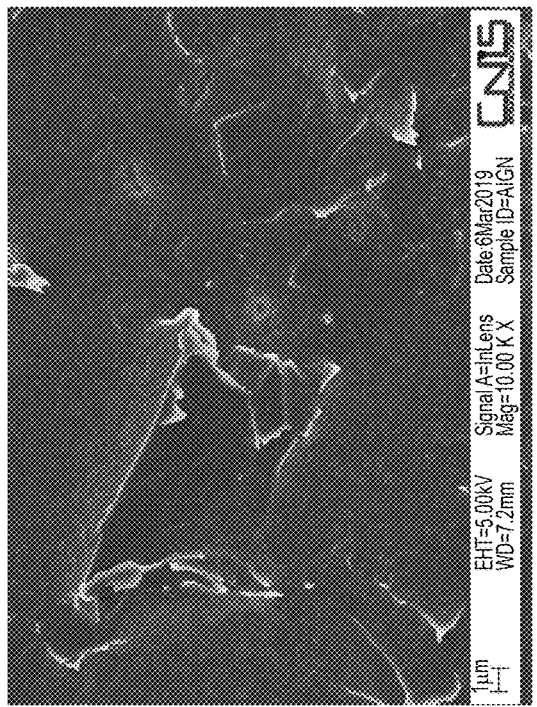
Figure 20:
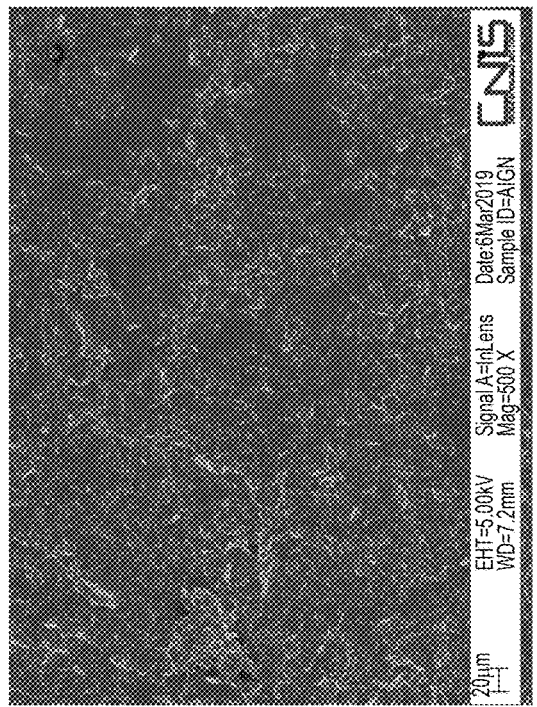
Figure 21:
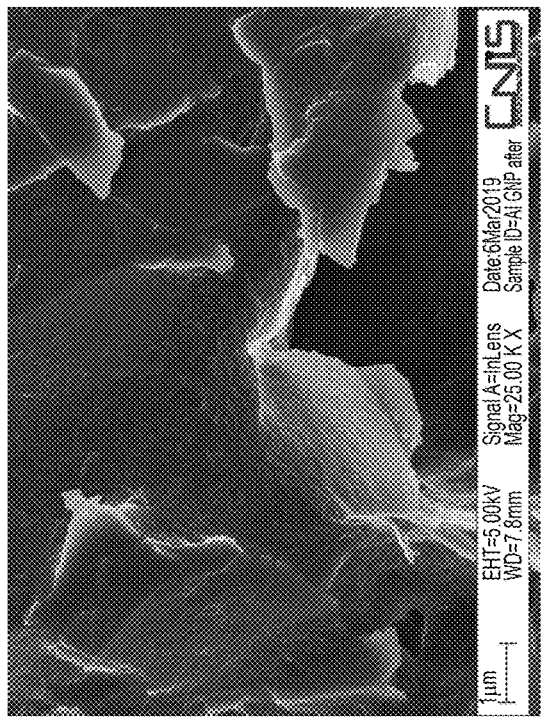
FIG. 21 shows the SEM images at different magnifications of the invention after testing with aqueous NaCl solutions and relative to Example 4.
Figure 21:
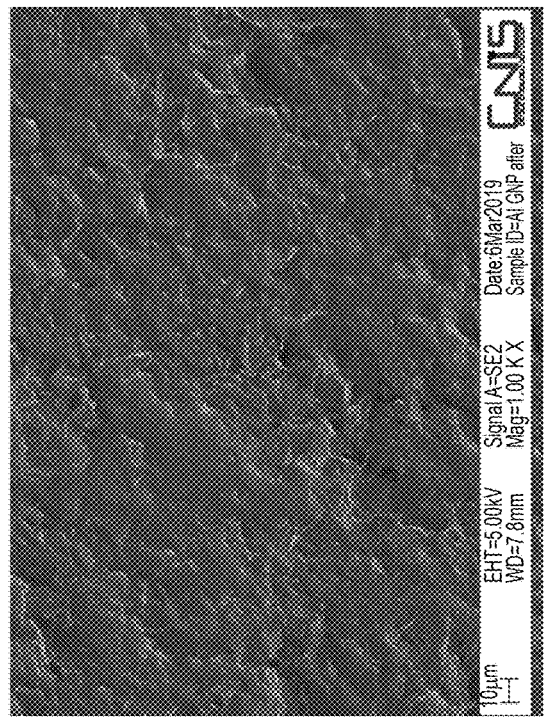
Figure 21:
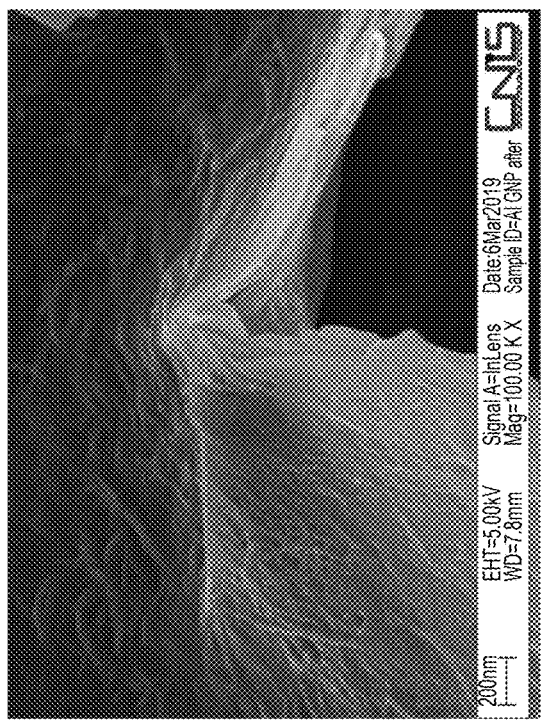
Figure 21:
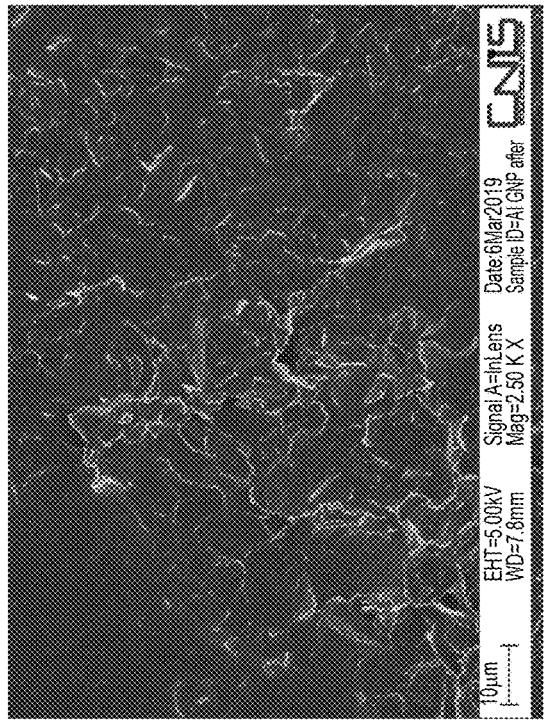
Figure 21:
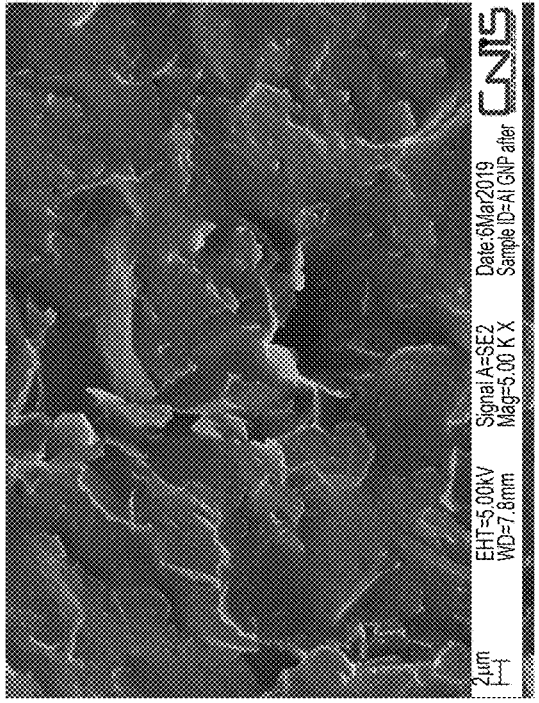
Figure 21:
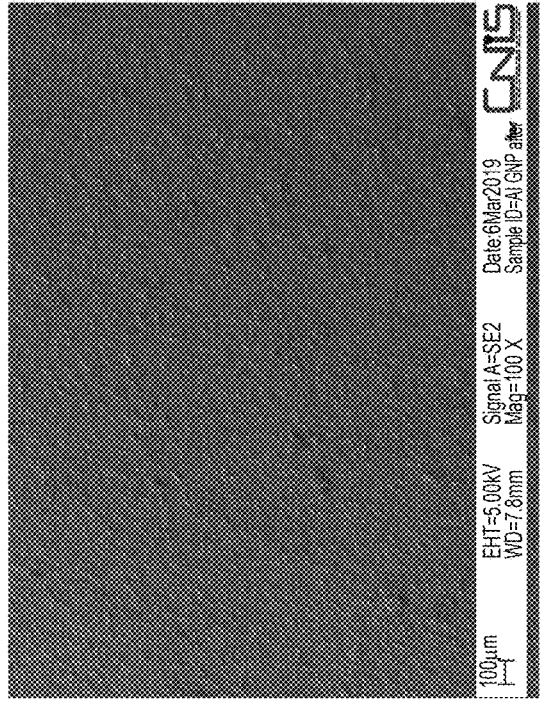
Figure 21:
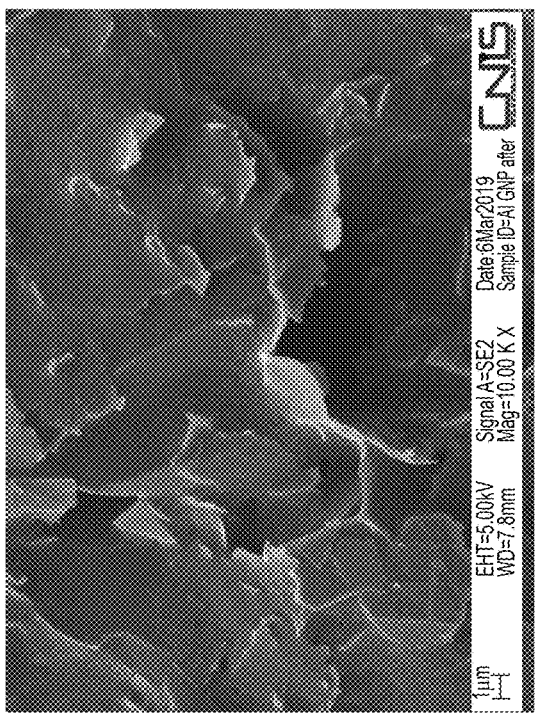
Figure 21:
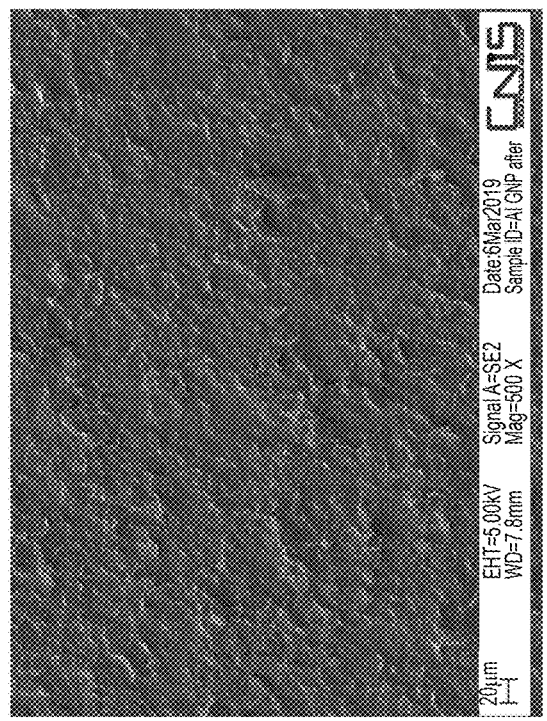

Morphological Characterization:

In order to verify any changes in the material following exposure to aqueous NaCl solutions, the sample was analyzed with an electron scanning microscope (SEM) at the Nanotechnologies Laboratory of Sapienza University of Rome. In particular, the sample was analyzed before and after the various tests. FIG. 20 shows the SEM images at different magnifications taken before the sample came into contact with the different aqueous NaCl solutions used for the characterization. Conversely, FIG. 21 shows the SEM images of the produced sample after the various characterizations described. It should be noted that the GNPs and metal nickel microparticles have good adhesion in the polymer matrix. It is also apparent that the morphology of the film does not change after the electrochemical test in saline solution.

Example 5—Multi-Composite Film Made with PVDF, GNP and Commercial Aluminum

The multi-composite polymer film made by way of explanation as described in the previous section and shown in FIG. 2 (b) was produced using a commercial aluminum sheet and loading the PVDF with an amount of GNP equal to 11% by weight of the PVDF.

The two electrodes incorporated in the polymer sheet produced are electrically contacted by silver paint, conductive epoxy glue containing silver and silver conductive wires.

The structure and morphology of the polymer film were analyzed using the field emission electron scanning microscope (FE-SEM) available at the Nanotechnology Laboratory of the Nanotechnology Research Centre applied at the Engineering Faculty of Sapienza University (CNIS).

Figure 22:
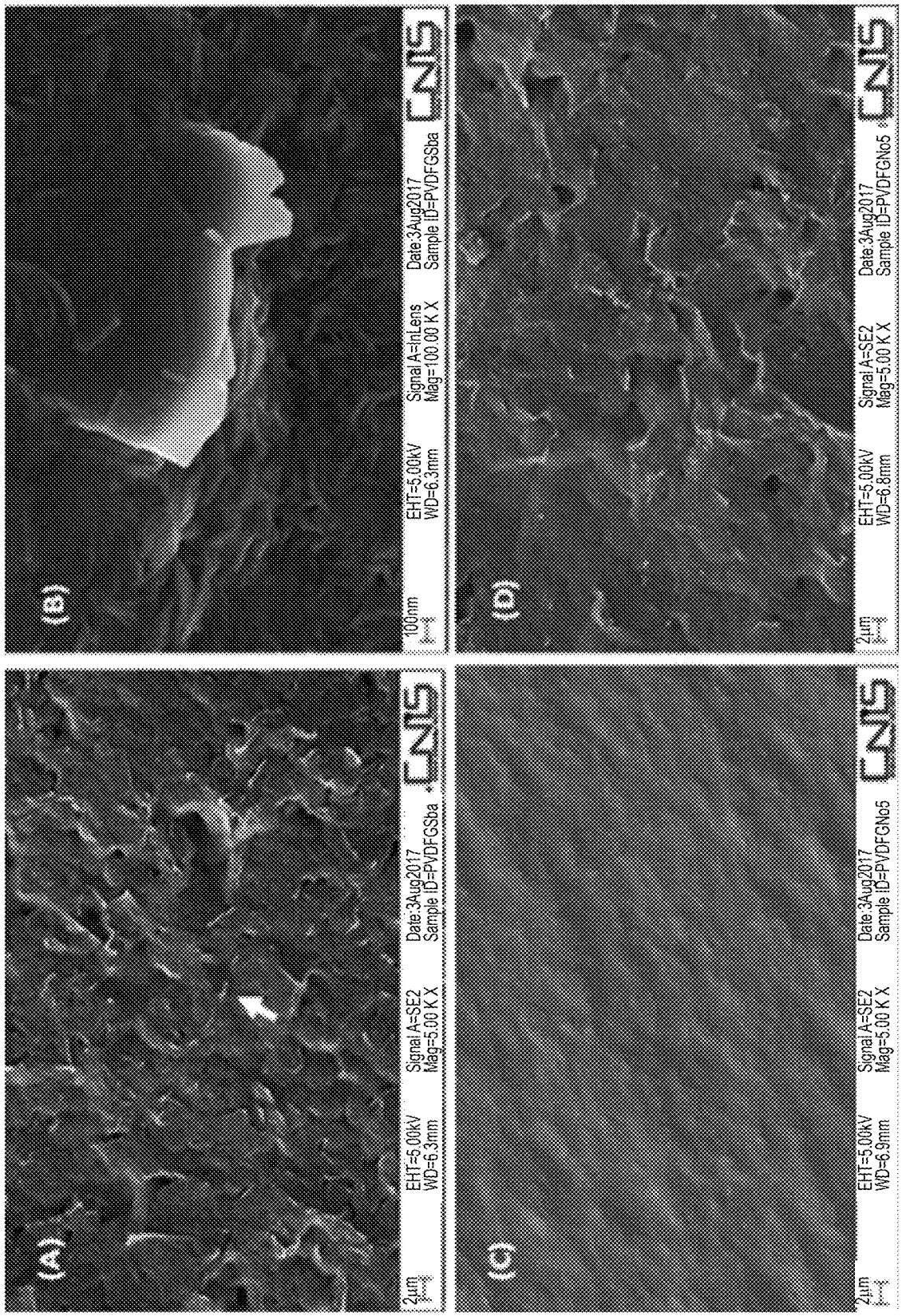
FIG. 22 shows the SEM images of the samples produced with a GNP content in the PVDF of 11% by weight relative to Example 5; in particular.

FIG. 22 shows the surfaces of the different sectors of the polymer film produced. The PVDF-GNP nanocomposite sector is obtained with a concentration of GNP equal to 11% by weight of PVDF. There is an excellent integration of the GNPs in the polymer matrix and the absence of porosity. It should also be noted that the aluminum element is perfectly covered on both sides by the polymer.

Figure 23:
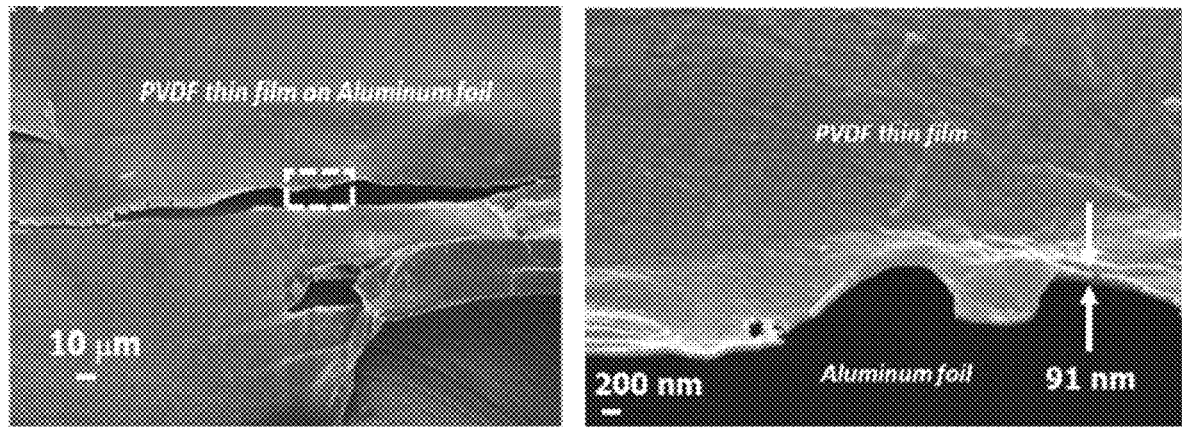
FIG. 23 shows the SEM images of hybrid polymer composite sheet relative to Example 5 produced using a commercial aluminum sheet, imposing a 30 µm thickness and loading the PVDF with an amount of GNP equal to 11% of the weight of the PVDF.

FIG. 23 shows the detail of the thin PVDF film covering the aluminum element, visible only at the specially created surface fractures. From the SEM image processing, it appears that the thin PVDF film has a thickness of about 91 nm.

Figure 24:
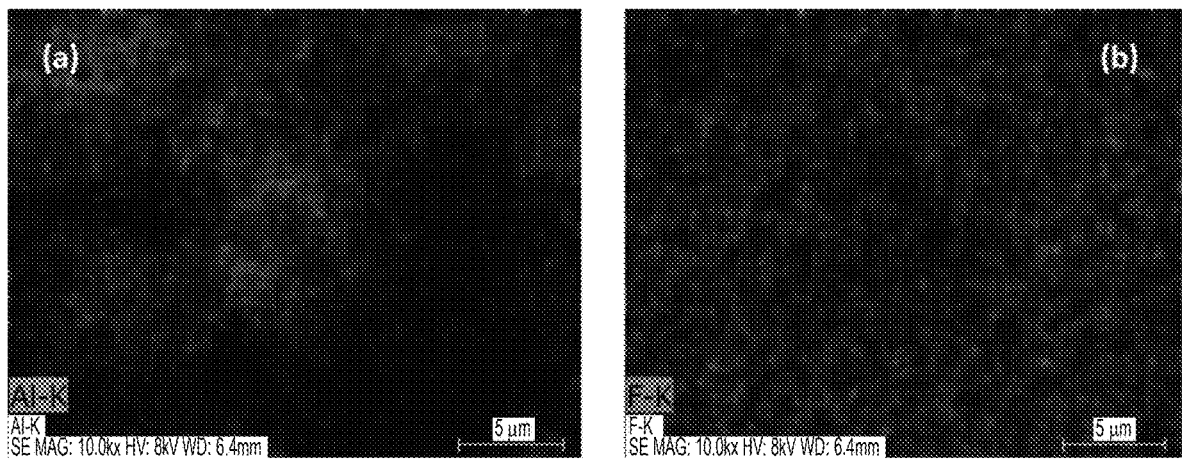
FIG. 24 shows EDX images of a hybrid composite film produced according to Example 5 using a commercial aluminum sheet, imposing a 30 µm thickness and loading the PVDF with an amount of GNP equal to 11% of the weight of the PVDF, respectively.

The PVDF film coating the aluminum sheet was also analyzed by X-ray energy dispersion spectroscopy (EDX). As can be deduced from the observation of FIG. 24 (a), which reports the mapping of the aluminum atoms, the presence of the commercial aluminum sheet is apparent. This confirms that the thickness of the PVDF film covering the aluminum is less than the micrometer (FIG. 24 (a)) and therefore the spectroscopic analysis is able to detect the presence of the aluminum below the thin polymer layer. FIG. 24 (b) further shows the uniform presence of fluorine atoms above the commercial aluminum sheet, indicating that the latter is entirely covered by the PVDF and thus perfectly protected against possible oxidative phenomena which can be activated if immersed in aqueous solution.

Example 6—Electrochemical Cell with Saline Solution for Low-Energy Application

Figure 25A:
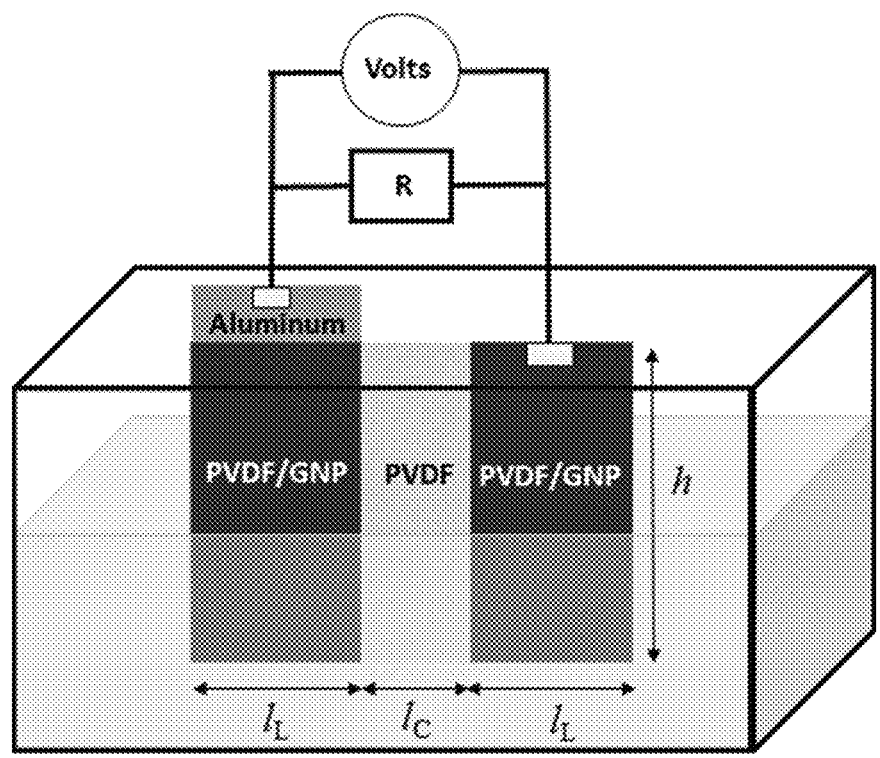
FIG. 25*a* shows the diagram of the set-up for measuring the voltage generated by the film object of the present invention and relative to Example 6.
Figure 25B:
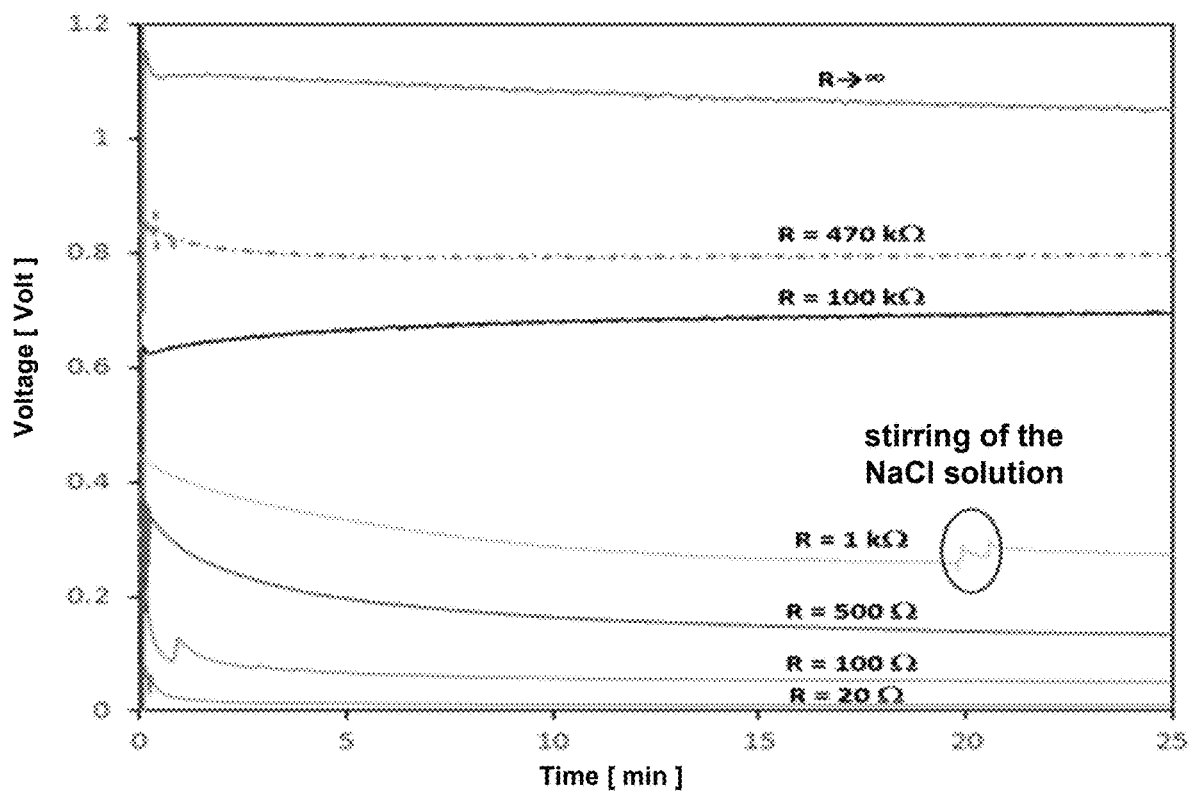
FIG. 25*b* shows the voltage produced as a function of time, inserting different resistors in parallel to the voltmeter for the invention according to Example 6.

For this application example of the invention, a membrane was produced the lateral (S1, S3) and central (S2) sectors of which have the same height of 5 cm and widths equal to 4 cm and 1 cm, respectively (with reference to FIG. 25(a): h=5 cm/L=4 cm and/c=1 cm). The hybrid composite film now described was immersed in an electrolytic solution by a height of 4 cm, thereby having for each of the two faces of each lateral sector an area of 4 cm×4 cm, directly exposed to the electrolyte. In particular, a solution of distilled water and 5.8% by weight pure sodium chloride was chosen. By means of a voltmeter connected to the hybrid film as shown in FIG. 25 (a), the voltage generated as a function of time was measured, connecting several resistors R in parallel to the voltmeter. In particular, the voltmeter was connected on one side directly to the aluminum sheet, on the other to the part not exposed to the electrolytic solution of the lateral PVDF sector loaded with GNP, by creating an area of 1 cm² in silver paint to which a silver conductor was connected by means of an epoxy glue.

Finally, for this application example, electrical resistors of variable value from 2012 to 470 kΩ were chosen. In all cases, an almost stable voltage signal was measured: the only fluctuations are observable at the beginning, when the film is immersed, or when the solution is stirred.

The measured voltage is shown as a function of time in FIG. 25 (b), where R→∞ indicates that no resistor was connected in parallel to the voltmeter.

Following the test carried out, the surface of the polymer sheet sectors which performed the function of anodic electrode (the one containing the aluminum sheet) and cathodic electrode (that in nanocomposite PVDF and GNP) was again analyzed.

Figure 26:
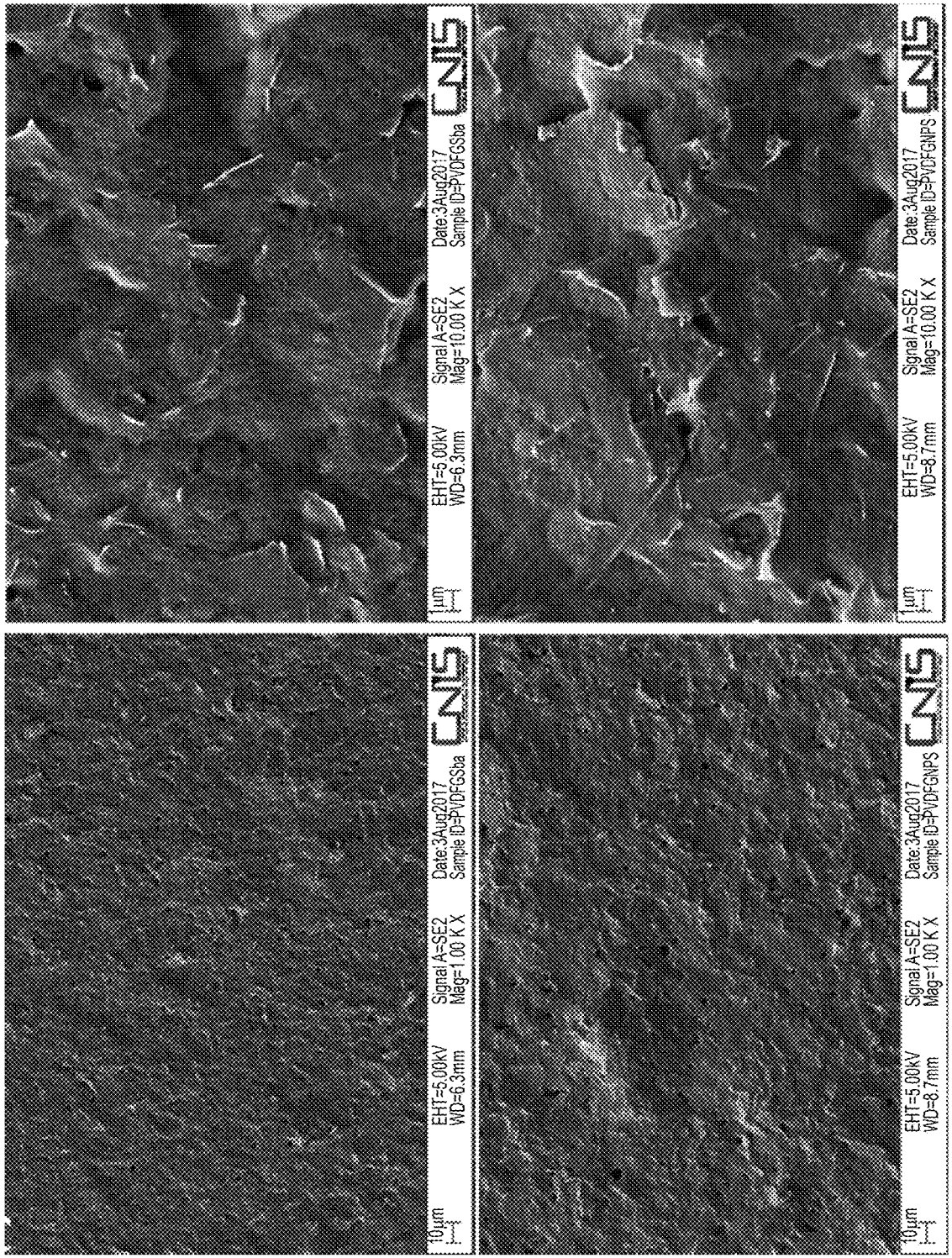
FIG. 26 shows the SEM images at different enlargements of the cathode electrode surface (PVDF nanopolymer composite sheet sector and 11% GNP by weight) before (A,B) and after (C,D) the test in saline solution relative to Example 6.
Figure 27A:
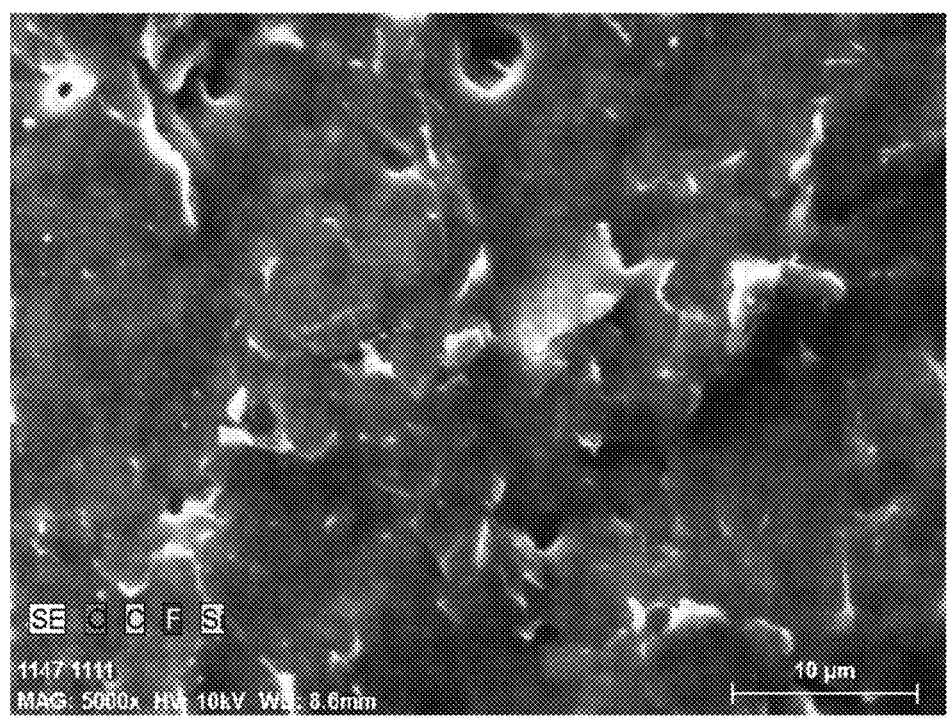
FIG. 27 shows the EDX mapping and compositional analysis of the surface of the PVDF and GNP nanocomposite sector, after the test in saline solution relative to Example 6.
Figure 27B:
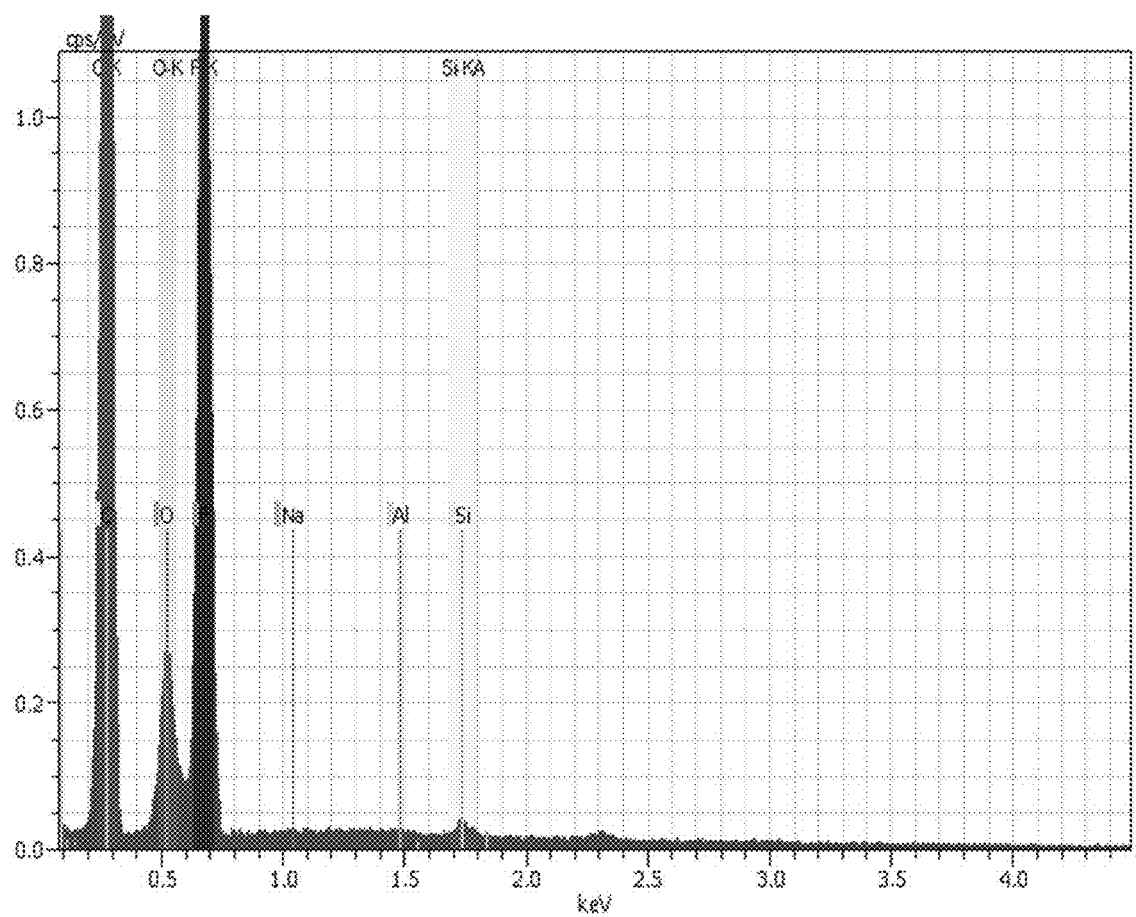

FIG. 26 shows the surface of the cathode before and after the electrochemical test in saline solution. It should be noted that the surface of the polymer film loaded with GNP did not change during the test. FIG. 27 shows the results of the EDX compositional analysis of the film surface performed after the test in saline solution.

Figure 28:
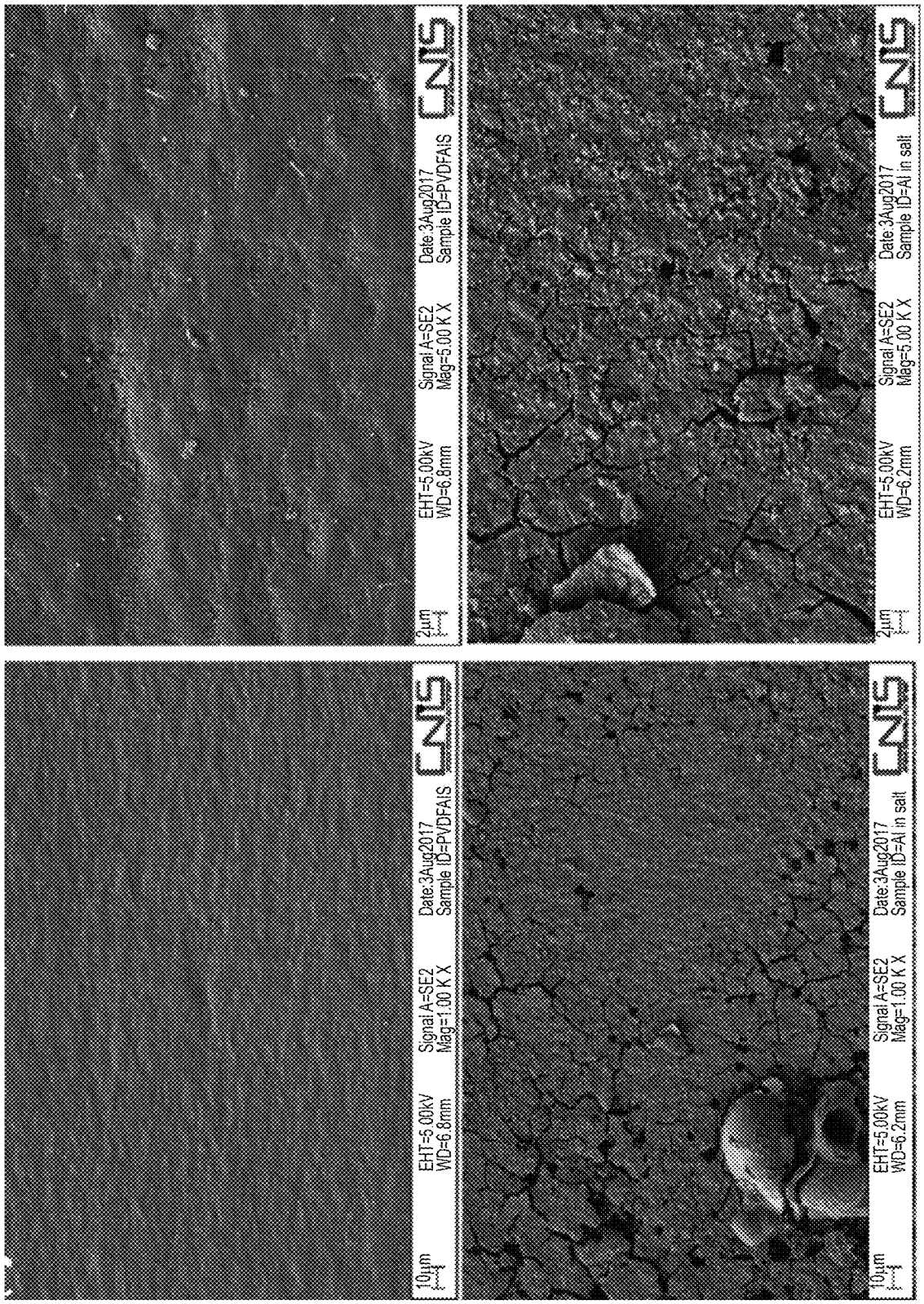
FIG. 28 shows the SEM images at different magnifications of the surface of the anodic electrode made with aluminum sheet entirely incorporated in PVDF-based polymer film as described in the present invention and in Example 6, seen from the side of the PVDF film, after the test in saline solution (A,B) and the SEM images at different magnifications of anodic electrode consisting of aluminum sheet after the test in saline solution where the effect of the electrode corrosion (C,D) is apparent.

FIG. 28 shows the surface of the anodic electrode consisting of aluminum sheet incorporated in the PVDF-based film after the test in saline solution (FIG. 28A, B). Unlike the case in which the same test is performed with an anodic electrode consisting of an unprotected aluminum sheet (FIGS. 28 C, D), the absence of aluminum corrosion phenomena is noted.

Figure 29:
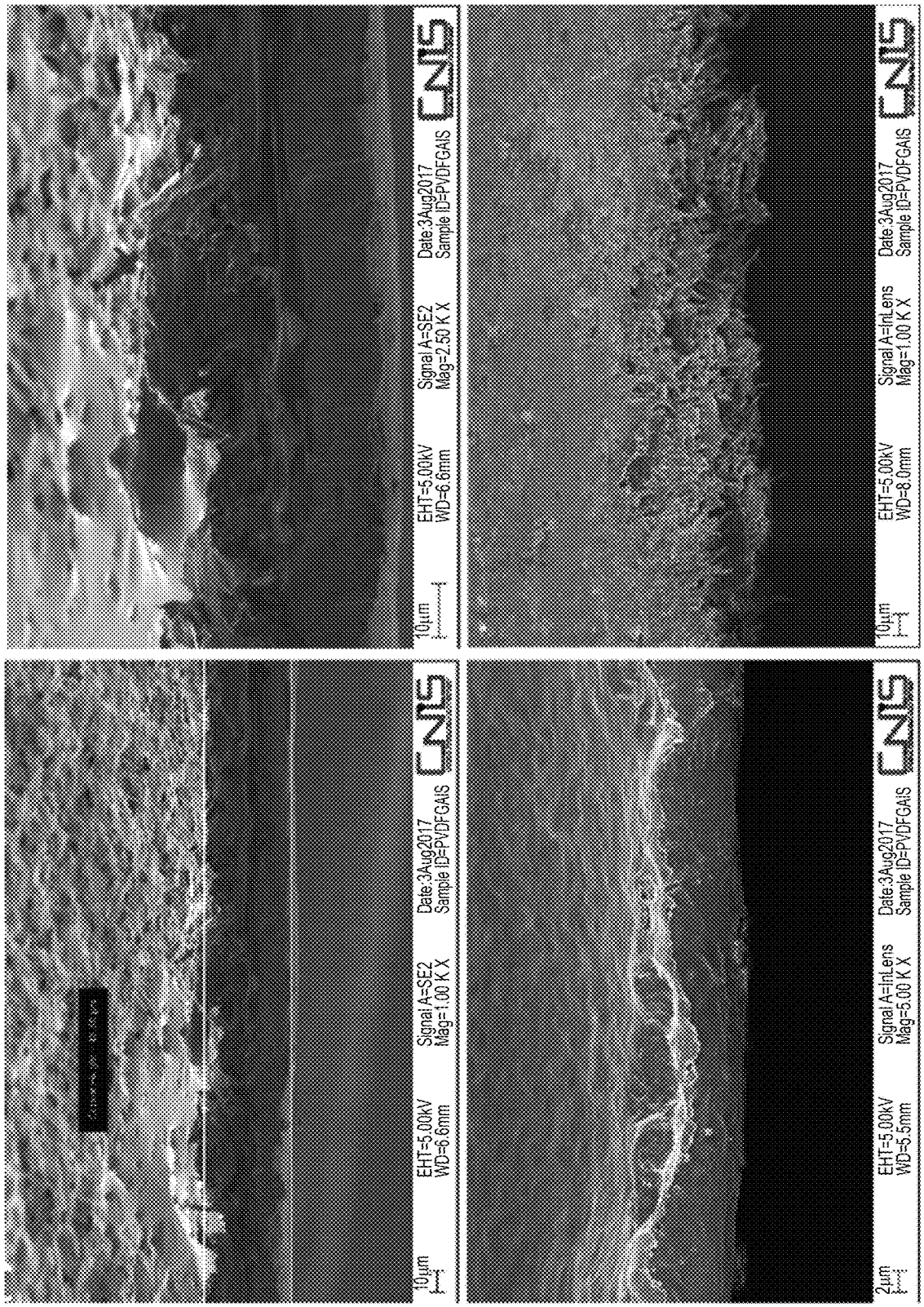
FIG. 29 shows the SEM images at different fracture edge magnifications of the different sectors of the polymer sheet object of the present invention according to Example 6, after electrochemical test in saline solution: (A,B,C) detail of the polymer sheet sector consisting of aluminum layer incorporated in PVDF-GNP nanocomposite (upper side in A and B) and thin PVDF film (lower side in A,B and upper side in C); (D) detail of the polymer sheet sector consisting of PVDF-GNP nanocomposite layer.

The absence of degradation of the sectors with electrode function of the polymer sheet object of the present invention is also demonstrated by the SEM images of FIG. 29, which show the section of the different sectors of the sheet after the electrochemical test in saline solution.

For example, the use of the invention for the production of electricity for low energy applications, can be used in signaling, lighting and rescue means.

The invention claimed is:

1. A multi-composite electrochemical cell consisting essentially of a thin polymer membrane comprising three different adjacent sectors, which are made of the same appropriately seamlessly modified polymer, incorporating in said polymer one or more conductive phases, or conductive fillers, and wherein:
   in the first sector, the polymer material incorporates graphene nanoplatelets and acts as a cathode;
   in the second sector, interposed between the other two, the polymer material acts as an insulating spacer;
   in the third sector, the polymer material incorporates graphene nanoplatelets and a metal filler or immersed metal contact rheophore, with negative standard reduction potential, and acts as an anode;
wherein said metal filler is in the form of dispersed powder or dispersed flakes, or of a thin sheet incorporated in the polymer.

2. The electrochemical cell according to claim 1, wherein said metal filler when present results in a different electrochemical potential for the two lateral sectors of the polymer membrane, said sectors acting as a cathode and as an anode, respectively, of the electrochemical cell in the presence of a conductive solution which connects them electrically.

3. The electrochemical cell according to claim 2, wherein when said first cathode sector and said third anode sector are electrically connected to each other by means of a conductive solution which touches them simultaneously acting as an electrolytic solution, a voltage is produced between said cathode and anode, the intensity of which depends on the concentration of ions in the conductive solution.

4. The electrochemical cell according to claim 2, wherein the polymer material is polyvinylidene fluoride.

5. The electrochemical cell according to claim 4, wherein said metal filler with negative standard reduction potential is Nickel or Aluminum.

6. The electrochemical cell according to claim 5, wherein said polymer membrane is self-standing, light, flexible and maneuverable, washable and reusable.

7. The electrochemical cell according to claim 1, wherein when said first cathode sector and said third anode sector are electrically connected to each other by means of a conductive solution which touches them simultaneously acting as an electrolytic solution, a voltage is produced between said cathode and anode, the intensity of which depends on the concentration of ions in the conductive solution.

8. The electrochemical cell according to claim 1, wherein the polymer material is polyvinylidene fluoride.

9. The electrochemical cell according to claim 1, wherein said metal filler with negative standard reduction potential is Nickel or Aluminum.

10. The electrochemical cell according to claim 1, wherein said polymer membrane is self-standing, light, flexible and maneuverable, washable and reusable.

11. A process of producing an electrolytic cell with polymer membrane wherein it includes using at least the following reagents, chemicals, and products:
   polyvinylidene fluoride,
   N, N-dimethylformamide,
   commercial metal powders or thin sheets,
   graphite intercalation compound,
and wherein it comprises the following steps:
(a) producing worm-like exfoliated graphite, or WEG, through thermal expansion of graphite intercalation compounds, said GIC compounds being subjected to a thermal shock at a temperature above 1000° C. for a time between 4 and 8 seconds, thus causing an increase in volume of about 200 times and complete reduction;
(b) dissolving a film of polyvinylidene fluoride PVDF in N, N-dimethylformamide by magnetic stirring, for a time period up to 4 hours, at a controlled temperature between 55° C. and 75° C.;
(c) partitioning the PVDF and DMF solution obtained from the previous step into two containers: a first container and a second container;
(d) adding the worm-like exfoliated graphite prepared in step (a), to the first container;
(e) homogenizing, through sonication, the compound resulting from the previous step, using an ultrasound processor set with a pulsed cycle (typically 1 sec on and 1 sec off) and for an execution time of at least fifteen minutes, thus ensuring the exfoliation of the WEGs and obtaining a suspension of GNP;
(f) obtaining, after sonication, two distinct mixtures: one consisting of PVDF+DMF only in the second container, the other of PVDF+DMF loaded with GNP in the first container;
(g) separating part of the mixture of PVDF and GNP from the first container in a third container and adding commercial metal powders or metal flakes thereto, mixed by stirring and/or ultrasonic bath, depending on the metal powders chosen;
(h) casting the three mixtures thus obtained: one consisting of PVDF only, another of PVDF with GNP, and a third one consisting of PVDF, GNP, and metal powders, on a mask appropriately provided to obtain a polymer membrane having three different adjacent sectors;
(i) treating the mask with the cast mixtures from the previous step, in an oven at 160° C. for a time period from 1 to 6 hours.

12. The process according to claim 11, wherein the dissolution step (b) occurs at the temperature of 65° C. for 2 hours.

* * * * *